United States Patent
Sharma

(10) Patent No.: US 8,798,753 B2
(45) Date of Patent: *Aug. 5, 2014

(54) DEVICE AND IMPLANTATION SYSTEM FOR ELECTRICAL STIMULATION OF BIOLOGICAL SYSTEMS

(71) Applicant: Endostim, Inc., St. Louis, MO (US)

(72) Inventor: Virender K. Sharma, Paradise Valley, AZ (US)

(73) Assignee: EndoStim, Inc., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/934,040

(22) Filed: Jul. 2, 2013

(65) Prior Publication Data

US 2014/0018657 A1    Jan. 16, 2014

Related U.S. Application Data

(63) Continuation of application No. 12/359,317, filed on Jan. 25, 2009, now Pat. No. 8,543,210.

(60) Provisional application No. 61/023,535, filed on Jan. 25, 2008.

(51) Int. Cl.
  *A61N 1/05* (2006.01)
  *A61B 5/00* (2006.01)
  *A61N 1/36* (2006.01)

(52) U.S. Cl.
  CPC ............ *A61B 5/6879* (2013.01); *A61N 1/0502* (2013.01); *A61N 1/0551* (2013.01); *A61N 1/05* (2013.01); *A61N 1/0558* (2013.01); *A61N 1/36007* (2013.01)
  USPC .............................. 607/40; 607/126; 607/128

(58) Field of Classification Search
  USPC .............................. 607/40, 126–131
  See application file for complete search history.

(56) References Cited

U.S. PATENT DOCUMENTS

| | | |
|---|---|---|
| 4,612,934 A | 9/1986 | Borkan |
| 5,117,827 A | 6/1992 | Stuebe |
| 5,231,988 A | 8/1993 | Wernicke |
| 5,263,480 A | 11/1993 | Wernicke |
| 5,292,344 A | 3/1994 | Douglas |
| 5,423,872 A | 6/1995 | Cigaina |
| 5,540,730 A | 7/1996 | Terry |
| 5,690,691 A | 11/1997 | Chen |
| 5,716,385 A | 2/1998 | Mittal |

(Continued)

FOREIGN PATENT DOCUMENTS

| | | |
|---|---|---|
| WO | 9853878 | 12/1998 |
| WO | 0061223 | 10/2000 |

(Continued)

OTHER PUBLICATIONS

EPO Search Report EP09704463, Jan. 10, 2011, Virender K. Sharma.

(Continued)

*Primary Examiner* — Joseph Dietrich
(74) *Attorney, Agent, or Firm* — Novel IP

(57) ABSTRACT

An implantable stimulation device for use in stimulation based treatments for diseases such as GERD or obesity is described. The device is provided with an anchoring unit which upon deployment assumes a shape optimized for the site of deployment. Sensing electrodes and stimulating electrodes in the device are also designed to assume a suitable shape upon deployment. A novel catheter is also provided for easy and expeditious deployment of the device.

13 Claims, 15 Drawing Sheets

(56) References Cited

U.S. PATENT DOCUMENTS

| | | |
|---|---|---|
| 5,836,994 A | 11/1998 | Bourgeois |
| 5,861,044 A | 1/1999 | Crenshaw |
| 6,041,258 A | 3/2000 | Cigaina |
| 6,091,992 A | 7/2000 | Bourgeois |
| 6,097,984 A | 8/2000 | Douglas |
| 6,216,039 B1 | 4/2001 | Bourgeois |
| 6,285,897 B1 | 9/2001 | Kilcoyne |
| 6,321,124 B1 | 11/2001 | Cigaina |
| 6,381,495 B1 | 4/2002 | Jenkins |
| 6,449,511 B1 | 9/2002 | Mintchev |
| 6,510,332 B1 | 1/2003 | Greenstein |
| 6,587,719 B1 | 7/2003 | Barrett |
| 6,591,137 B1 | 7/2003 | Fischell |
| 6,611,715 B1 | 8/2003 | Boveja |
| 6,615,084 B1 | 9/2003 | Cigaina |
| 6,678,561 B2 | 1/2004 | Forsell |
| 6,749,607 B2 | 6/2004 | Edwards |
| 6,754,536 B2 | 6/2004 | Swoyer |
| 6,760,626 B1 | 7/2004 | Boveja |
| 6,826,428 B1 | 11/2004 | Chen |
| 6,832,114 B1 | 12/2004 | Whitehurst |
| 6,879,859 B1 | 4/2005 | Boveja |
| 6,901,295 B2 | 5/2005 | Sharma |
| 7,006,871 B1 | 2/2006 | Darvish |
| 7,016,735 B2 | 3/2006 | Imran |
| 7,054,689 B1 | 5/2006 | Whitehurst |
| 7,054,690 B2 | 5/2006 | Imran |
| 7,076,305 B2 | 7/2006 | Imran |
| 7,076,306 B2 | 7/2006 | Marchal |
| 7,087,053 B2 | 8/2006 | Vanney |
| 7,114,502 B2 | 10/2006 | Schulman |
| 7,120,498 B2 | 10/2006 | Imran |
| 7,146,216 B2 | 12/2006 | Bumm |
| 7,167,750 B2 | 1/2007 | Knudson |
| 7,177,693 B2 | 2/2007 | Starkebaum |
| 7,200,443 B2 | 4/2007 | Faul |
| 7,263,405 B2 | 8/2007 | Boveja |
| 7,299,091 B2 | 11/2007 | Barrett |
| 7,310,557 B2 | 12/2007 | Maschino |
| 7,340,306 B2 | 3/2008 | Barrett |
| 7,343,201 B2 | 3/2008 | Mintchev |
| 7,444,183 B2 | 10/2008 | Knudson |
| 7,620,454 B2 | 11/2009 | Dinsmoor |
| 7,702,395 B2 | 4/2010 | Towe |
| 7,702,934 B2 | 4/2010 | Imran |
| 7,729,771 B2 | 6/2010 | Knudson |
| 7,734,355 B2 | 6/2010 | Cohen |
| 7,738,961 B2 | 6/2010 | Sharma |
| 7,742,818 B2 | 6/2010 | Dinsmoor |
| 7,794,425 B2 | 9/2010 | Gobel |
| 7,835,796 B2 | 11/2010 | Maschino |
| 7,899,540 B2 | 3/2011 | Maschino |
| 7,914,468 B2 | 3/2011 | Shalon |
| 7,962,214 B2 | 6/2011 | Byerman |
| 8,160,709 B2 | 4/2012 | Soffer |
| 8,282,561 B2 | 10/2012 | Towe |
| 8,447,403 B2 | 5/2013 | Sharma |
| 8,447,404 B2 | 5/2013 | Sharma |
| 8,452,407 B2 | 5/2013 | Whitehurst |
| 2001/0041831 A1 | 11/2001 | Starkweather |
| 2002/0161414 A1 | 10/2002 | Flesler |
| 2002/0165589 A1 | 11/2002 | Imran |
| 2003/0014086 A1 | 1/2003 | Sharma |
| 2003/0078633 A1 | 4/2003 | Firlik |
| 2003/0144708 A1 | 7/2003 | Starkebaum |
| 2004/0012088 A1 | 1/2004 | Fukasawa |
| 2004/0015201 A1 | 1/2004 | Greenstein |
| 2004/0024428 A1 | 2/2004 | Barrett |
| 2004/0039427 A1 | 2/2004 | Barrett |
| 2004/0044376 A1 | 3/2004 | Flesler |
| 2004/0059393 A1 | 3/2004 | Policker |
| 2004/0073453 A1 | 4/2004 | Nenov |
| 2004/0116977 A1 | 6/2004 | Finch |
| 2004/0172088 A1 | 9/2004 | Knudson |
| 2004/0186544 A1 | 9/2004 | King |
| 2004/0193229 A1 | 9/2004 | Starkebaum |
| 2004/0243182 A1 | 12/2004 | Cohen |
| 2005/0049655 A1 | 3/2005 | Boveja |
| 2005/0065571 A1 | 3/2005 | Imran |
| 2005/0070974 A1 | 3/2005 | Knudson |
| 2005/0075678 A1 | 4/2005 | Faul |
| 2005/0090873 A1 | 4/2005 | Imran |
| 2005/0131486 A1 | 6/2005 | Boveja |
| 2005/0137643 A1 | 6/2005 | Mintchev |
| 2005/0137644 A1 | 6/2005 | Boveja |
| 2005/0143787 A1 | 6/2005 | Boveja |
| 2005/0149141 A1 | 7/2005 | Starkebaum |
| 2005/0149142 A1 | 7/2005 | Starkebaum |
| 2005/0149146 A1 | 7/2005 | Boveja |
| 2005/0222637 A1 | 10/2005 | Chen |
| 2005/0251219 A1 | 11/2005 | Evans |
| 2006/0036293 A1 | 2/2006 | Whitehurst |
| 2006/0064037 A1 | 3/2006 | Shalon |
| 2006/0074459 A1 | 4/2006 | Flesler |
| 2006/0095077 A1 | 5/2006 | Tronnes |
| 2006/0106442 A1 | 5/2006 | Richardson |
| 2006/0116736 A1 | 6/2006 | DiLorenzo |
| 2006/0167498 A1 | 7/2006 | DiLorenzo |
| 2006/0206160 A1 | 9/2006 | Cigaina |
| 2006/0218011 A1 | 9/2006 | Walker |
| 2006/0247722 A1 | 11/2006 | Maschino |
| 2007/0016274 A1 | 1/2007 | Boveja |
| 2007/0106337 A1 | 5/2007 | Errico |
| 2007/0162084 A1 | 7/2007 | Chen |
| 2007/0162085 A1 | 7/2007 | DiLorenzo |
| 2007/0238942 A1 | 10/2007 | Baylor |
| 2007/0239248 A1 | 10/2007 | Hastings |
| 2008/0021512 A1 | 1/2008 | Knudson |
| 2008/0039904 A1 | 2/2008 | Bulkes |
| 2008/0086179 A1 | 4/2008 | Sharma |
| 2008/0147137 A1 | 6/2008 | Cohen |
| 2008/0154191 A1 | 6/2008 | Gobel |
| 2008/0195171 A1 | 8/2008 | Sharma |
| 2008/0208355 A1 | 8/2008 | Stack |
| 2009/0030475 A1 | 1/2009 | Brynelsen |
| 2009/0069803 A1 | 3/2009 | Starkebaum |
| 2009/0132001 A1 | 5/2009 | Soffer |
| 2009/0204063 A1 | 8/2009 | Policker |
| 2009/0264951 A1 | 10/2009 | Sharma |
| 2009/0281553 A1 | 11/2009 | Kalloo |
| 2010/0198039 A1 | 8/2010 | Towe |
| 2010/0324432 A1 | 12/2010 | Bjoerling |
| 2011/0004266 A1 | 1/2011 | Sharma |
| 2011/0071589 A1 | 3/2011 | Starkebaum |
| 2011/0307027 A1 | 12/2011 | Sharma |
| 2011/0307028 A1 | 12/2011 | Sharma |
| 2012/0232610 A1 | 9/2012 | Soffer |
| 2012/0265103 A1 | 10/2012 | Policker |
| 2013/0178912 A1 | 7/2013 | Sharma |

FOREIGN PATENT DOCUMENTS

| | | |
|---|---|---|
| WO | 0061224 | 10/2000 |
| WO | 0243467 | 6/2002 |
| WO | 2005051486 A1 | 9/2005 |
| WO | 2007137026 | 11/2007 |
| WO | 2009114008 A1 | 9/2009 |
| WO | 2010027963 | 3/2010 |
| WO | 2010135634 | 11/2010 |
| WO | 2012151449 | 11/2012 |

OTHER PUBLICATIONS

Ellis, et al., 'The Prevention of Experimentally Induced Reflux by Electrical Stimulation of the Distal Esophagus', American Journal of Surgery, vol. 115, Apr. 1968, 482-487.

Kahrilas et al., 'Impact of Fundoplication on Bolus Transit Across Esophagogastric Junction', American Physiological Society, 1998, 1386-1393.

Lund et al., 'Electrical Stimulation of Esophageal Smooth Muscle and Effects of Antagonists', American Journal of Physiology, vol. 217, No. 5, Nov. 1969, 1369-1374.

(56) References Cited

OTHER PUBLICATIONS

Stein et al., 'Three-dimensional Imaging of the Lower Esophageal Sphincter in Gastroesophageal Reflux Disease,' Annual Meeting of the American Surgical Association, Apr. 11-13, 1991, 374-383.
Gonzalez et al., 'Different Responsiveness of Excitatory and Inhibitory Enteric Motor Neurons in the Human Esophagus to Electrical Field Stimulation and to Nicotine', Am J Physiol Gastrointest Liver Physiol, 287:G299-G306, 2004.
Kamath et al., 'Neurocardiac and Cerebral Responses Evoked by Esophageal Vago-Afferent Stimulation in Humans: Effects of Varying Intensities', Cardiovascular Research, 40 (1998) 591-599.
Christensen et al., 'Physiologic Specialization at Esophagogastric Junction in Three Species', American Journal of Physiology, vol. 225, No. 6, Dec. 1973, 1265-1270.
Summary of Neurostimulation Systems Features, Advanced Neuromodulation Systems (ANS) home page, accessed on May 31, 2007 at http://web.archive.org/web/20040211224857/www.ans-medical.com/patients/WhichSystemIsBest/SumOfNeurostimulation.html.
International Search Report for PCT/US2007/068907.
International Search Report for PCT/US2012/036408.
International Search Report for PCT/US2012/033695.
International Search Report for PCT/US2011/027243.
International Search Report for PCT/US2012/053576.

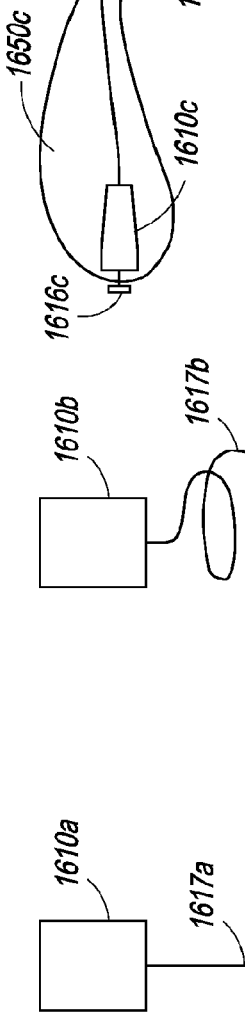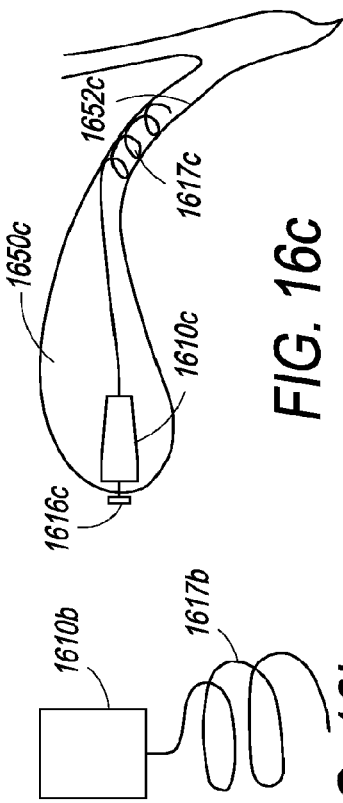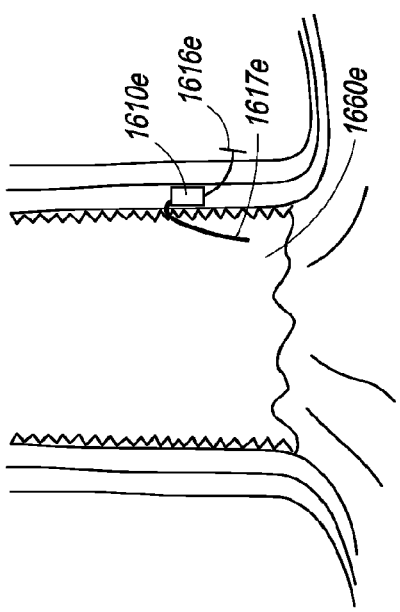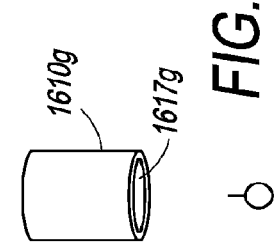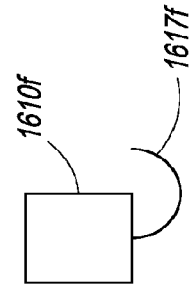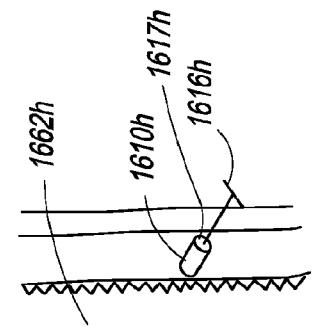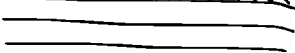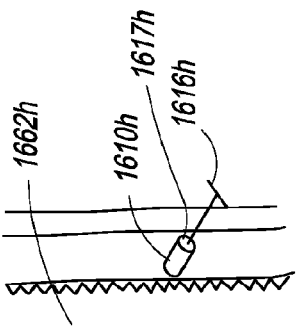

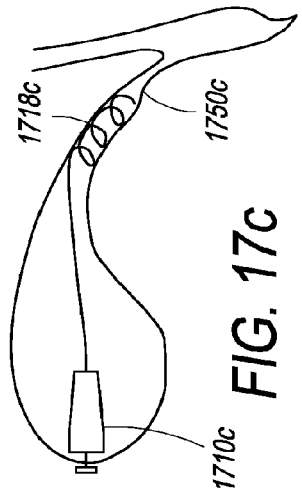
FIG. 17c
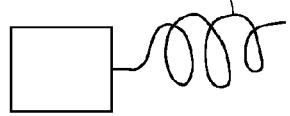
FIG. 17b
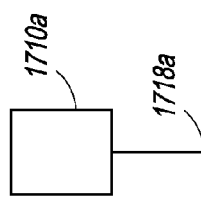
FIG. 17a
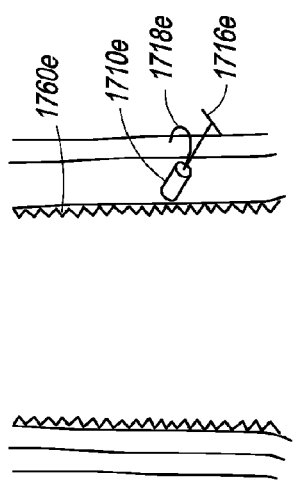
FIG. 17f
FIG. 17e
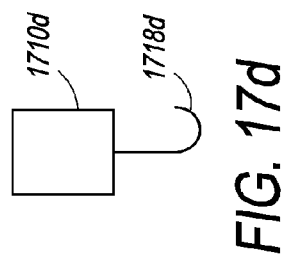
FIG. 17d
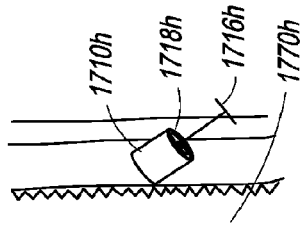
FIG. 17h
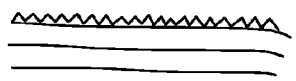
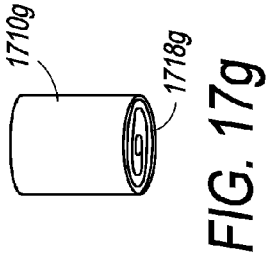
FIG. 17g

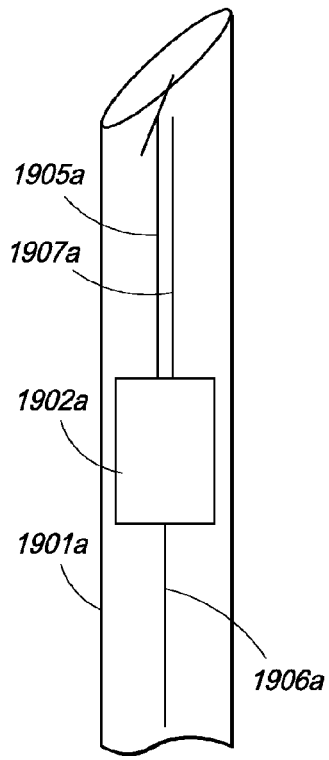 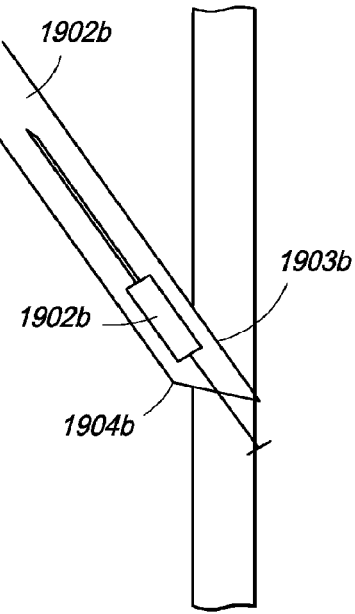 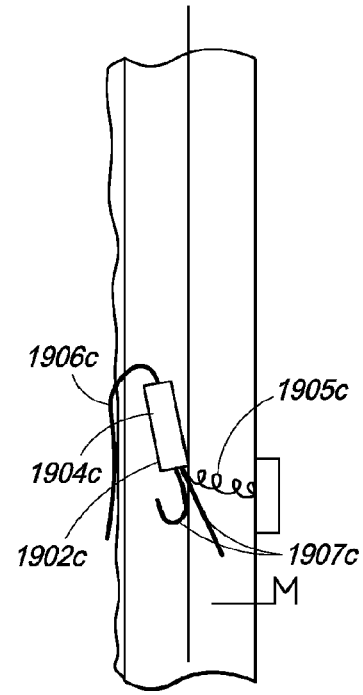
FIG. 19a　　　　FIG. 19b　　　　FIG. 19c
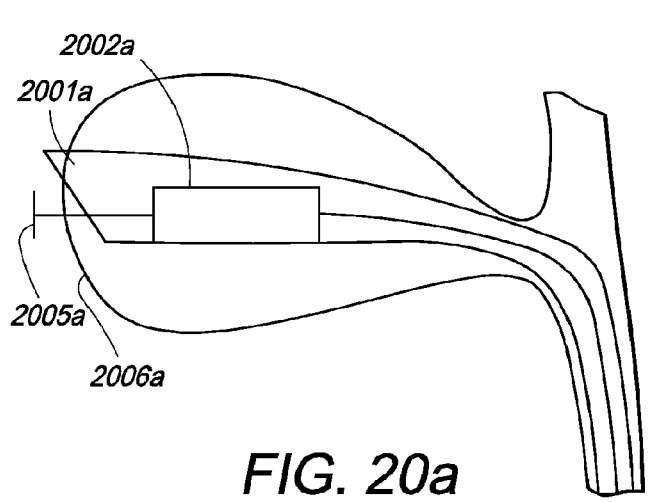 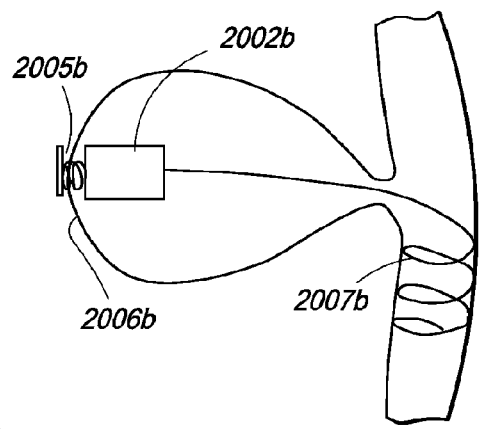
FIG. 20a　　　　　　FIG. 20b

DEVICE AND IMPLANTATION SYSTEM FOR ELECTRICAL STIMULATION OF BIOLOGICAL SYSTEMS

CROSS REFERENCE

This application relies on U.S. patent application Ser. No. 12/359,317, issued as U.S. Pat. No. 8,543,210, which relies on U.S. Provisional Application No. 61/023,535 for priority that is herein incorporated by reference.

FIELD OF THE INVENTION

This invention relates generally to a method and apparatus for electrical stimulation of the biological systems. More particularly, this invention relates to a method and apparatus for treating a condition by electrically stimulating a portion of the gastrointestinal system.

BACKGROUND OF THE INVENTION

Gastro-esophageal reflux disease (GERD) is a common problem and is expensive to manage in both primary and secondary care settings. This condition results from exposure of esophageal mucosa to gastric acid as the acid refluxes from the stomach into the esophagus. The acid damages the esophageal mucosa resulting in heartburn, ulcers, bleeding, and scarring, and long term complications such as Barrett's esophagus (pre-cancerous esophageal lining) and adeno-cancer of the esophagus. Transient relaxation of the lower esophageal sphincter (LES) is believed to be the primary mechanism of the disease although the underlying cause remains uncertain.

Lifestyle advice and antacid therapy is advocated as first line treatment for the disease. However since most patients with moderate to severe cases of GERD do not respond adequately to these first-line measures and need further treatment, therefore other alternatives including pharmacological, endoscopic, and surgical treatments are employed.

The most commonly employed pharmacological treatment is daily use of H2 receptor antagonists (H2RAs) or proton-pump inhibitors (PPIs) for acid suppression. Since gastro-esophageal reflux disease usually relapses once drug therapy is discontinued, most patients with the disease, therefore, need long-term drug therapy. However, daily use of PPIs or H2RAs is not universally effective in the relief of GERD symptoms or as maintenance therapy. Additionally, not all patients are comfortable with the concept of having to take daily or intermittent medication for the rest of their lives and many are interested in nonpharmacological options for managing their reflux disease.

Several endoscopic procedures for the treatment of GERD are being tried. These procedures can be divided into three approaches—endoscopic suturing where stitches are inserted in the gastric cardia to plicate and strengthen the lower esophageal sphincter; the endoscopic application of radio-frequency to the lower esophagus; and the injection of bulking agents into the muscle layer of the distal esophagus. These procedures, however, are not without their risks, besides being technically demanding and involving a long procedure time. As a result, these procedures have largely been discontinued.

Open surgical or laparoscopic fundoplication is also used to correct the cause of the disease. However, surgical procedures suffer from the disadvantages that they are associated with significant morbidity and small but finite mortality. Moreover, long-term follow-up with patients treated by surgery suggests that many patients continue to need acid suppressive medication. There is also no convincing evidence that fundoplication reduces the risk of esophageal adenocarcinoma in the long term.

Besides GERD, obesity is a common condition and a major public health problem in developed nations including the United States of America. Today, 64.5% of American adults, about 127 million people, are either overweight or obese. Data suggest that 300,000 Americans die prematurely from obesity-related complications each year. Many children are overweight or obese in the United States; hence, the steady increase in the number of overweight Americans is expected to continue. It has been estimated that obesity costs the United States approximately $100 billion annually in direct and indirect health care expenses and in lost productivity. This trend is also apparent in many other developed countries.

Morbid obesity is defined as possessing either a body weight more than 100 pounds greater than normal or a body mass index (BMI) greater than 40 kg/m$^2$. Approximately 5% of the U.S. population meets at least one of these definitions. A BMI greater than 30 kg/m$^2$ is associated with significant co-morbidities. Morbid obesity is associated with many diseases and disorders including, for example, diabetes, hypertension, heart attacks, strokes, dyslipidemia, sleep apnea, Pickwickian Syndrome, asthma, lower back and disc disease, weight-bearing osteo-arthritis of the hips, knees, ankles and feet, thrombophlebitis and pulmonary emboli, intertriginous dermatitis, urinary stress incontinence, gastroesophageal reflux disease (GERD), gallstones, and sclerosis and carcinoma of the liver. In women, infertility, cancer of the uterus, and cancer of the breast are also associated with morbid obesity. Taken together, the diseases associated with morbid obesity markedly reduce the odds of attaining an average lifespan and raise annual mortality in affected people by a factor of 10 or more.

Current treatments for obesity include diet, exercise, behavioral treatments, medications, surgery (open and laproscopic) and endoscopic devices. Also, additional treatments for obesity are currently being evaluated in drug clinical trials. However, a high efficacy pharmaceutical treatment has not yet been developed. Further, short-term and long-term side effects of pharmaceutical treatments may concern consumers, pharmaceutical providers, and/or their insurers. Generally, diet or drug therapy programs have been consistency disappointing and fail to bring about significant, sustained weight loss in the majority of morbidly obese people.

Currently, most morbid obesity operations are, or include, gastric restrictive procedures, involving the creation of a small (e.g., 15-35 mL) upper gastric pouch that drains through a small outlet (e.g., 0.75-1.2 cm), setting in motion the body's satiety mechanism. About 15% of morbid obesity operations done in the United States involve gastric restrictive surgery combined with a malabsorptive procedure. Typical malabsorptive procedures divide small intestinal flow into a biliary-pancreatic conduit and a food conduit. Potential long-term problems with surgical procedures, including those seen after any abdominal procedure, are notorious and can include, for example, ventral hernia and small bowel obstruction. In addition, long-term problems specific to bariatric procedures can include, for example, gastric outlet obstruction, marginal ulceration, protein malnutrition, and vitamin deficiency.

Other surgical strategies for treating obesity include endoscopic procedures, many of which are still in development. Endoscopically placed gastric balloons restrict gastric volume and result in satiety with smaller meals. Endoscopic procedures and devices to produce gastric pouch and gastrojejunal anastomosis to replicate laporoscopic procedures are also in development. These procedures, however, are not without risks.

Gastric electric stimulation (GES) is another procedure that is currently in clinical trial. GES employs an implantable, pacemaker-like device to deliver low-level electrical stimulation to the stomach. The procedure involves the surgeon suturing electrical leads to the outer lining of the stomach wall. The leads are then connected to the device, which is implanted just under the skin in the abdomen. Using an external programmer that communicates with the device, the surgeon establishes the level of electrical stimulation appropriate for the patient. The Transcend® implantable gastric stimulation device, manufactured by Transneuronix Corporation, is currently available in Europe for treatment of obesity.

In another example, Medtronic offers for sale and use the Enterra™ Therapy, which is indicated for the treatment of chronic nausea and vomiting associated with gastroparesis when conventional drug therapies are not effective. The Enterra™ Therapy uses mild electrical pulses to stimulate the stomach. According to Medtronic, this electrical stimulation helps control the symptoms associated with gastroparesis including nausea and vomiting.

U.S. Pat. No. 6,901,295, issued to the inventor, describes an implantable apparatus for electrical stimulation of the lower esophageal sphincter (LES). It relies on sensing certain physiological changes in the esophagus, such as changes in esophageal pH, to detect acid reflux, which is required for generating electrical stimulation in order to abort the episode of acid reflux through the LES into the esophagus. pH sensing is conventionally used to detect GERD, in the form of a 24 hour pH test. Additionally impedance pH testing is also used to detect GERD and using pattern recognition, pH of the refluxate could be assessed using impedance pH testing.

There is still a need for a safe and effective method of treatment that can help alleviate symptoms of GERD in the long term, without adversely affecting the quality of life of the patients. In addition, there is still a need for minimally invasive and effective treatment for obesity. Moreover, there is not only a need for better devices in stimulation based therapies, but there is also a need for a safe and minimally invasive method and system that enables easy and expeditious deployment of such devices at any desired location in the body. Most of the currently available devices are available for surgical or laparoscopic implantation and suffer from common problem of pocket infection, lead dislodgment or fracture.

Furthermore, there is still a need for a device and method for implanting microstimulator devices within the gastrointestinal system. Stimulators are typically implanted surgically. U.S. Pat. Nos. 7,076,305 and 7,016,735 disclose an implantable device for electrically stimulating the stomach wall to cause gastric motility or otherwise treat gastrointestinal related disorders. The device is implanted using an endoscope. As designed, deployment can only occur in the stomach lumen and requires the use of a protective overtube for repeated passage of endoscope, passing the device into the stomach and to prevent instruments and devices from inadvertently dropping into the trachea and prevent bacterial contamination which can happen with multiple passes of the instruments. Overtubes are cumbersome, technically difficult, and associated with complications such as perforation, gastrointestinal wall tears and bleeding.

SUMMARY OF THE INVENTION

In one embodiment, the present invention is directed to an implantable device for stimulating the smooth muscles or nerves inside the body, comprising a) a stimulator for generating pulses and delivering the generated pulses to said smooth muscles or nerves through a stimulating electrode; b) a sensor module with a sensing electrode for detecting a change in a physiological parameters; c) an anchoring unit attached to said stimulator, wherein said anchoring unit has a pre-deployment shape and a post deployment shape and wherein said post deployment shape is different than the pre-deployment shape; d) a power source; and e) a microcontroller for instructing the stimulator to selectively generate said pulses. The implant site can be in any physical location, including the walls of one or more organs.

Optionally, the anchoring unit is further used to facilitate puncture at the implant site for deployment of said device. Upon deployment of said device into an implant site, a shape of said anchoring unit changes to a predetermined shape, said predetermined shape being determined according to the implant site. The shape of said anchoring unit changes to any one of a T-bar, a ship anchor, a spiral disc, a hook, a spiral loop, a loop or any freeform shape or non-linear shape capable of anchoring. The device may comprise more than one anchoring unit and said more than one anchoring unit each assume same or different shapes upon deployment. Upon deployment of said device into an implant site, a shape of said sensing electrode may change to a predetermined shape, said predetermined shape being determined according to the implant site. The shape of said sensing electrode changes to any one of a spiral shape, an acute angular shape, or a hook. The sensing electrode or sensor maybe configured as a disk attached to one surface of said device. The shape of said stimulating electrode may change to a predetermined shape, said predetermined shape being determined according to the implant site. The shape of said stimulating electrode changes to any one of a spiral shape, a hook, a double hook or a loop. The stimulating electrode maybe configured as a disk attached to one surface of said device. The anchoring unit maybe used to deliver said stimulus pulses to the nerve or the smooth muscles. The sensing electrode maybe used to deliver said stimulus pulses to the nerve or the smooth muscles as well as to detect changes in physiological parameters of said smooth muscles in response to said stimulus pulses. The anchoring unit may also used to detect changes in physiological parameters of said smooth muscles in response to said stimulus pulses. One electrode unit may comprise the stimulating electrode, the sensing electrode, and the anchoring unit. One or all of these units could be made of shape memory alloys. The physiological parameters include at least one of pH, pressure, peristalsis, temperature, impedance, motion, flow, electrical activity, chemical activity, hormonal activity, muscular activity and neural activity.

In another embodiment, the present invention is directed to a catheter system for containing, delivering, and implanting a device for stimulating the smooth muscles inside the body, comprising a) a catheter having a housing further comprising a stimulator for generating pulses and delivering the generated pulses to said nerve or smooth muscles through a stimulating electrode, a sensor module with a sensor or sensing electrode for detecting a change in physiological parameters, a power source, and a microcontroller for instructing the stimulator to selectively generate said pulses; and b) an anchoring unit attached to said stimulator.

Optionally, the anchoring unit foreshortens upon deployment of said device in the intestinal wall or smooth muscles to pull the device deeper into said intestinal wall or smooth muscles. Upon deployment of said device into an implant site, a shape of said anchoring unit changes to a predetermined shape, said predetermined shape being determined according to the implant site. The shape of said anchoring unit changes to any one of a T-bar, a ship anchor, a spiral disc, a hook, a club, a spiral loop, a loop or any freeform shape capable of anchoring.

BRIEF DESCRIPTION OF THE DRAWINGS

These and other objects and advantages of the present invention will become more fully apparent from the following detailed description when read in conjunction with the accompanying drawings with like reference numerals indicating corresponding parts through-out, wherein:

FIG. 16a illustrates a first exemplary configuration of the sensing electrode;

FIG. 16b illustrates a second exemplary configuration of the sensing electrode;

FIG. 16c illustrates a third exemplary configuration of the sensing electrode;

FIG. 16d illustrates a fourth exemplary configuration of the sensing electrode;

FIG. 16e illustrates a fifth exemplary configuration of the sensing electrode;

FIG. 16f illustrates a sixth exemplary configuration of the sensing electrode;

FIG. 16g illustrates a seventh exemplary configuration of the sensing electrode;

FIG. 16h illustrates an eighth exemplary configuration of the sensing electrode;

FIG. 17a illustrates a first exemplary configuration of the stimulating electrode;

FIG. 17b illustrates a second exemplary configuration of the stimulating electrode;

FIG. 17c illustrates a third exemplary configuration of the stimulating electrode;

FIG. 17d illustrates a fourth exemplary configuration of the stimulating electrode;

FIG. 17e illustrates a fifth exemplary configuration of the stimulating electrode;

FIG. 17f illustrates a sixth exemplary configuration of the stimulating electrode;

FIG. 17g illustrates a seventh exemplary configuration of the stimulating electrode;

FIG. 17h illustrates an eighth exemplary configuration of the stimulating electrode;

FIG. 19a illustrates a first step in an exemplary procedure for endoscopic deployment of the device into the LES;

FIG. 19b illustrates a second step in an exemplary procedure for endoscopic deployment of the device into the LES;

FIG. 19c illustrates a third step in an exemplary procedure for endoscopic deployment of the device into the LES;

FIG. 20a illustrates a first step in an exemplary procedure for endoscopic deployment of the device into the gallbladder; and FIG. 20b illustrates a second step in an exemplary procedure for endoscopic deployment of the device into the gallbladder.

DETAILED DESCRIPTION OF THE INVENTION

The present invention is directed toward a novel programmable implantable electro-medical device for the treatment of various neuro-muscular disorders, including gastro-esophageal reflux disease (GERD) and obesity. The electro-medical device of the present invention employs implantable microstimulators that can be implanted with minimal invasiveness in the gastrointestinal system. The stimulation patterns of the device can be altered to treat other conditions such as pancreatico-biliary stimulation or stimulating the lower esophageal sphincter when a person swallows to curtail food intake and thereby treat obesity. It should further be appreciated that the present device is capable of stimulating all smooth muscle, not limited to GI smooth muscles. The present application further incorporates by reference U.S. Pat. No. 6,901,295, PCT/US08/56479, and U.S. patent application Ser. Nos. 12/030,222 and 11/539,645.

Figure 1:
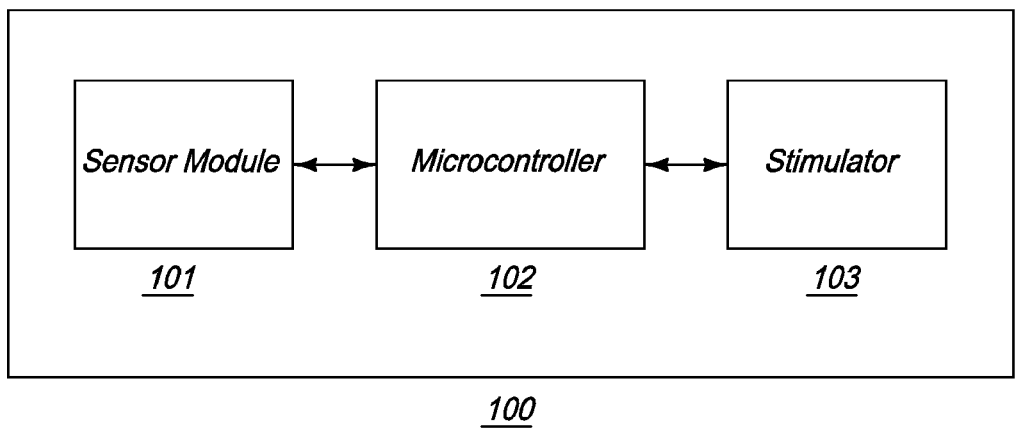
FIG. 1 is an overall block diagram of certain modules of the present invention.

Referring to FIG. 1, an overall block diagram illustrating the major components of the device of the present invention is shown. The device comprises three main units—a sensor module 101, a microcontroller 102 and a stimulator 103. The sensor module 101 comprises electrodes for sensing peristaltic flow, anti-peristaltic flow or reflux of gastric contents in the esophagus. On sensing the anti-peristaltic flow, the sensor module 101 provides this information to the microcontroller 102, which in turn activates the stimulator 103 to provide the required electrical stimulus that prevents the abnormal flow or reflux of gastric contents. In another embodiment, the sensor module 101 senses peristaltic flow of food from the esophagus into the stomach. On sensing the peristaltic flow, the sensor module 101 provides this information to the microcontroller 102, which in turn activates the stimulator 103 to provide the required electrical stimulus that prevents the flow of food from esophagus into stomach thus curtailing feeding. The sensor module 101, the microcontroller 102 and the stimulator 103 can communicate with each other using wired or wireless communication.

Figure 2:
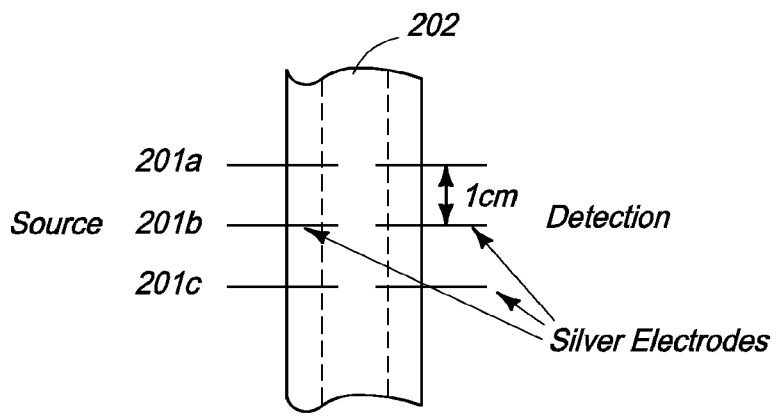
FIG. 2 is a schematic illustration of an exemplary arrangement of electrodes of the sensor module.

Referring to FIG. 2, an exemplary arrangement of electrodes of the sensor module is shown. The sensor module consists of three pairs of electrodes 201a, 201b, and 201c placed across the esophagus 202. In order to minimize the risk of rejection by the body, biocompatible electrodes such as gold, silver, platinum, titanium, or nitinol are used. Each pair of electrodes is placed at least 1 mm away from the nearest pair. As substances pass through the esophagus, it causes a change in impedance between the electrode pairs, and this forms the basis of detection of esophageal peristalsis or flow and its direction. The impedance across the esophagus is sensed by sending an ac voltage signal (2V p-p) and measuring the current, and the impedance is used to compute the speed of the esophageal flow. Depending on the electrode pair that senses the change in impedance first, the direction of flow can be determined. Thus if the electrode pair 201a detects a change in impedance first, followed by the pair 201b and then by 201c, it implies that the flow is a normal swallow, that is, substances are passing down from the esophagus into the stomach. However, if the order of sensing in the electrodes is reversed, that is, electrode pair 201c is the first to detect a change in impedance in the esophagus, it implies that the flow is anti-peristaltic and indicates a reflux event from the stomach into the esophagus. It should be appreciated that other sensors, including electrical, pressure, photo, thermal and chemical, can be used in place of, or in combination with, the impedance sensors.

In a patient with GERD, when anti-peristaltic flow is sensed by the sensor electrodes, the stimulator is activated to provide the required stimulus to the muscles of the lower esophageal sphincter (LES). The LES acts as a barrier between the esophagus and the stomach; applying electrical stimulus to the LES muscles causes them to contract and prevent the abnormal flow or reflux of gastric contents into the esophagus.

In addition, applying principal component analysis algorithms to perform signal analysis and data processing and using pattern recognition techniques, the nature of the reflux (acidic or alkaline) and the chemical composition of the reflux can be analyzed in real time. This data can then be used to help in modulate the stimulus and establish stimulation patterns.

In a patient with obesity, when peristaltic flow is sensed by the sensor electrodes, the stimulator is activated to provide the required stimulus to the muscles of the esophagus or lower esophageal sphincter (LES). The LES acts as a barrier between the esophagus and the stomach; applying electrical stimulus to the LES muscles causes them to contract and prevent the flow of food from the esophagus into the stomach thus controlling the intake of food.

In addition, applying principal component analysis algorithms to perform signal analysis and data processing and using pattern recognition techniques, the nature of the bolus and the chemical composition of the bolus can be analyzed in real time. This data can then be used to modulate the stimulus and establish stimulation patterns.

Figure 3:
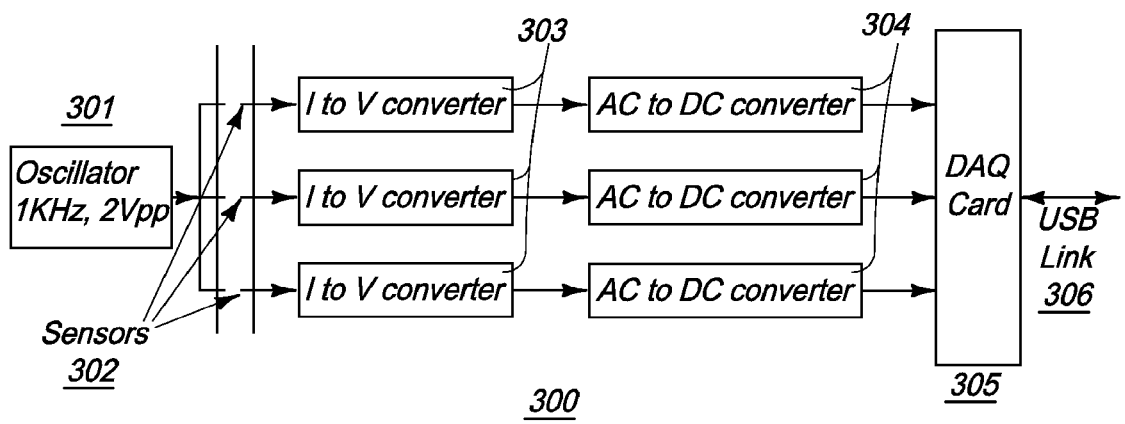
FIG. 3 is a schematic illustration of the major components comprising the sensor module of the present invention.

FIG. 3 illustrates the major components and the working of the sensor module. The sensor module 300 comprises an oscillator 301, which in one embodiment, is a Wein bridge oscillator producing a sinusoidal waveform of 1 KHz, 2 Vpp. The sinusoidal waveform thus produced is then applied to the electrode system (sensors) 302 directly, which senses the change in current through the medium to determine the change in impedance, as mentioned previously. The sensed current is then converted into voltage using three current to voltage (I to V) converters 303, one for each electrode pair. Since the output of the I to V converters 303 is still sinusoidal, it needs to be converted into DC using AC to DC converters 304. The DC output is fed to the microcontroller (not shown in this figure) through a data acquisition (DAQ) card 305. The microcontroller checks whether the voltage is above or below the threshold and determines the impedance in accordance with the voltage signal. As shown in FIG. 3, signals from the sensor module are fed to the microcontroller using a USB link 306. Alternatively, the signals may be sent to the microcontroller in a wireless fashion using an RF link, a wireless link (Bluetooth or other protocol), an ultrasonic link, a thermal link, a magnetic, an electromagnetic or an optical link.

Figure 4:
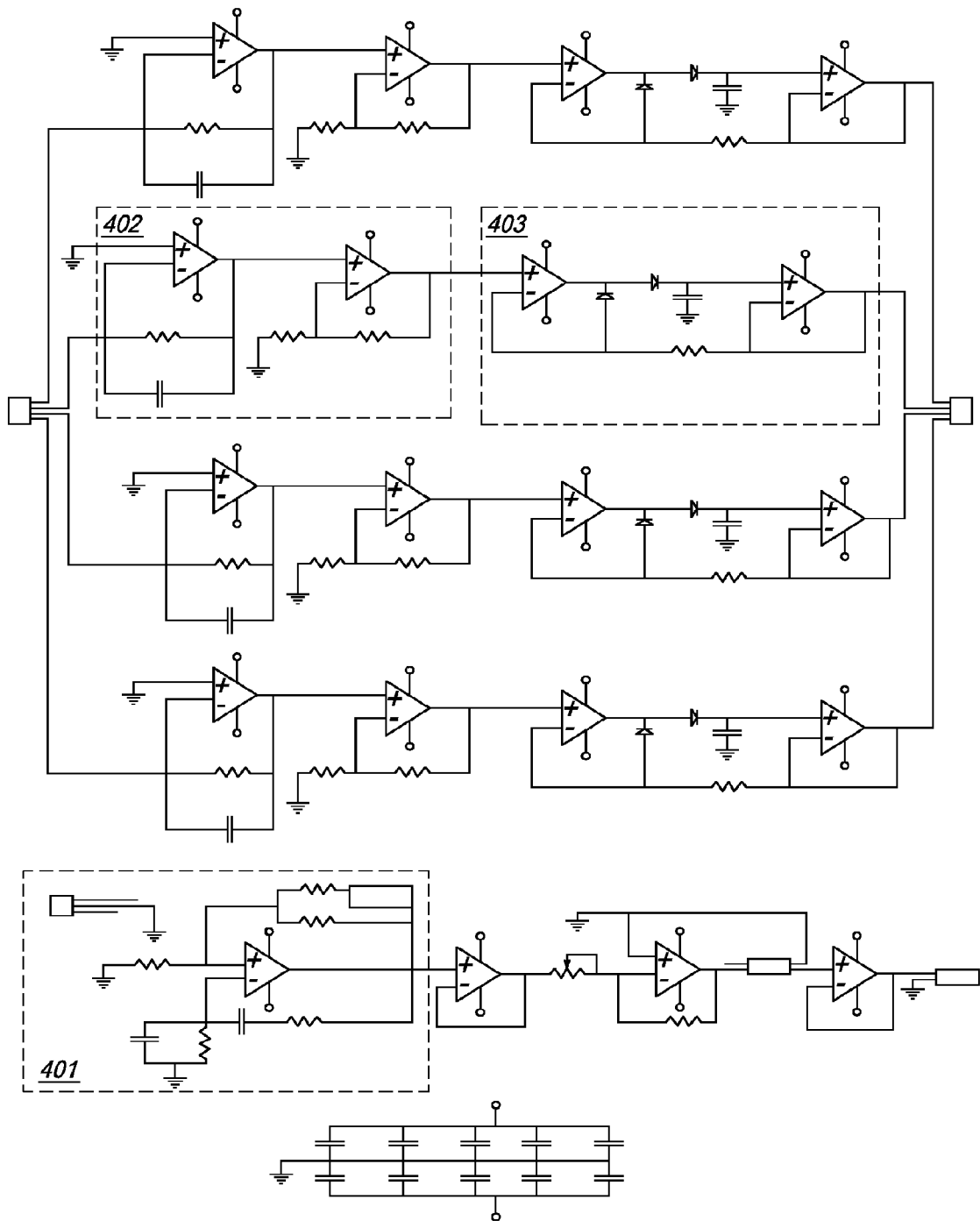
FIG. 4 is a detailed circuit diagram of the sensor module of the present invention.

The detailed circuit diagram for the sensor module is shown in FIG. 4. Block 401 in FIG. 4 shows the circuit details for the oscillator (301 of FIG. 3), while block 402 represents the circuit details for current to voltage converter (303 of FIG. 3) and block 403 represents AC to DC converter (304 of FIG. 3).

Figure 5:
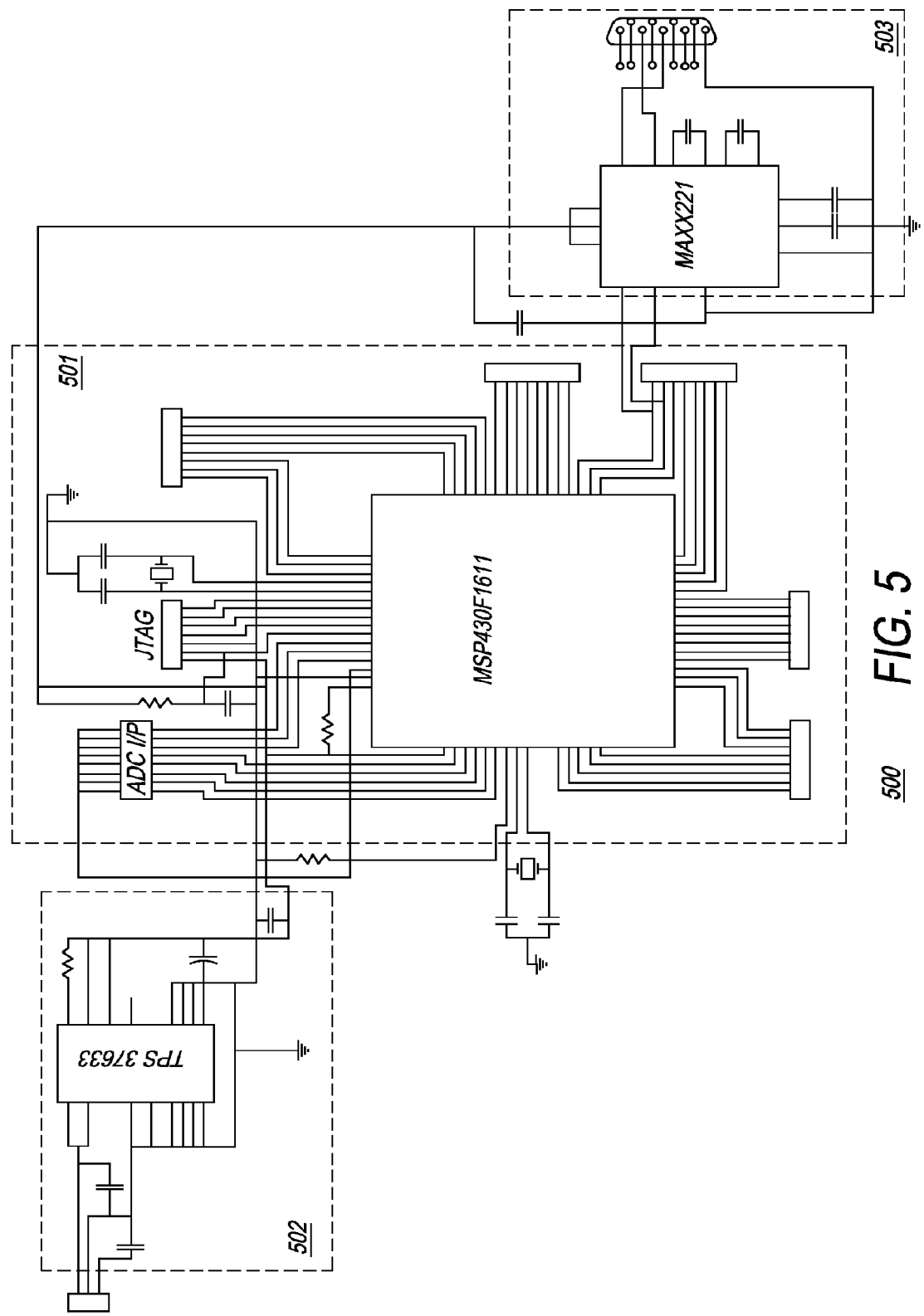
FIG. 5 is a detailed circuit diagram of the microcontroller unit of the present invention.

FIG. 5 illustrates a detailed circuit diagram for the microcontroller unit of the present invention. The microcontroller unit 500 consists of the microcontroller 501, a power management unit 502, and a level shifter unit 503. The microcontroller unit is designed to be portable, which can remotely (wirelessly) communicate with the sensor module and the stimulator. For this application, any suitable microcontroller 501 may be chosen. In one embodiment, a microcontroller from MSP430 family of Texas Instruments is used. Built around a 16-bit CPU, the MSP430 is designed for low cost, low power consumption embedded applications, and its architecture is particularly well suited for wireless RF or battery powered applications.

The power management unit 502 is used to convert output voltage from the power supply to the specified level of operating voltage of the microcontroller 501 (and its peripherals).

The microcontroller unit can be programmed using a computer such that it controls the stimulator to produce electrical pulses of varying shape, duration and frequency so as to produce the desired contractions in the LES or any other smooth muscle in the body. The interaction between microcontroller unit 500 and a computer for programming purposes is enabled by the level shifter unit 503 which converts UART data standard to RS232 level to enable communication through the serial port of the computer. Alternatively, communication may be carried out through the computer's USB link or in a wireless manner, using any suitable wireless standard. The microcontroller unit 500 is also provided with a JTAG port to facilitate programming and flash emulation. Additionally, the microcontroller unit is provided with six 8-bit General purpose I/O ports. Of these, two I/O pins are used for the indication of peristalsis and anti-peristalsis. The rest of the ports may be used for interfacing with other devices, such as a monitor.

Features of the microcontroller which help in achieving a simple yet effective design for the device of the present invention include:

Low Supply-Voltage Range—In one embodiment the range is between 1.8 V-3.6V.
Ultralow-Power Consumption, including a Standby Mode and Five Power-Saving Modes.
16-Bit RISC Architecture, with 125-ns Instruction Cycle Time.
Supply Voltage Supervisor/Monitor with Programmable Level Detection.

The microcontroller is also provided with sufficient inbuilt memory (RAM as well as flash memory) for storing the programs required for the present application. The microcontroller can also store physiological data from the sensor which can be wirelessly interrogated and used to custom program the device to meet specific patient's need.

As used in the present invention, the stimulator is an electrophysiological stimulator capable of producing a pulse train to stimulate specific muscles resulting in the contraction of those muscles. This stimulation helps to correct any transient or permanent changes in the lower esophageal sphincter (LES) which might, for example, occur due to incompetence of the LES, transient LES relaxation, impaired expulsion of gastric reflux from the esophagus, or a hiatal hernia. Similarly stimulation from the microstimulator can be used to modify or alter the contractility of any smooth muscle in the body to achieve any desired effect. For example, a stimulation from the microstimulator applied to the biliary system can cause the biliary system to contract thus altering the flow of biliary secretions into the intestinal tract.

With the transient or permanent changes in the muscle tone, the LES loses the tendency to contract which would otherwise prevent the reflux of the gastric contents into the esophagus. The current stimulator of the present invention stimulates the LES to contract and prevent the acid reflux into the esophagus, whenever the sensing module senses onset of anti-peristaltic flow of gastric contents. In one embodiment, the duration and/or frequency of the electrical pulses produced by are determined on the basis of the speed or directionality of esophageal flow detected by the sensing module. No stimulus is provided on sensing normal peristaltic flow.

In another application to treat obesity, the current stimulator of the present invention stimulates the LES to contract and prevent passage of food from the esophagus into the stomach producing the uncomfortable sensation of dysphagia, whenever the sensing module senses peristaltic flow associated with a swallow. The stimulator could be programmed to start stimulating the LES after a fixed duration after the onset of swallows based on patient's desired caloric intake. Alternatively, the stimulator can be triggered by the patient.

Figure 6:
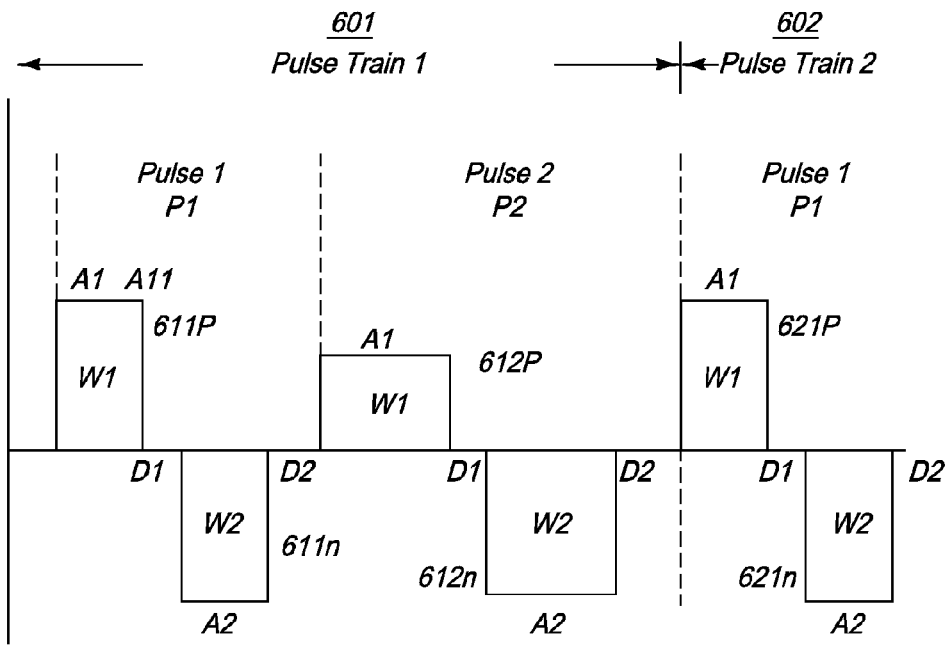
FIG. 6 is a schematic illustration of an exemplary waveform of pulses generated by the stimulator of the present invention.

FIG. 6 illustrates an exemplary waveform of pulses generated by the stimulator of the present invention. Referring to FIG. 6, the exemplary waveform comprises two pulse trains—Pulse Train 1 601 and Pulse Train 2 602. The pulse trains comprise of positive as well as negative pulses. A negative pulse is automatically generated by the stimulator along with a positive pulse to remove the polarization of the electrodes. Thus in FIG. 6, Pulse Train 1 601 comprises two positive pulse 611p and 612p, and their corresponding negative pulses 611n and 612n. Pulse Train 1 601 is followed by Pulse Train 2 602, with the two pulse trains being essentially repetitions of the similar pulse groups. However in the FIG. 6, only the first positive pulse 621p and its corresponding negative pulse 621n are shown. The amplitude (in mA) of current for each of the positive pulses 611p, 612p and 621p in FIG. 6 is represented by A1 and the width or pulse duration in msec for each of the positive pulses is represented by W1. Similarly A2 represents the amplitude for each of the negative pulses 611n, 612n, and 621n, while W2 represents the pulse duration for each of the negative pulses. Depending upon the requirements, there can be delays denoted by D1 between each positive and negative pulse, and D2 between each negative and positive pulse. For the first positive and negative pulse 611p and 611n respectively, the amplitude and pulse width are equal. That is, for 611p and 611n, A1=A2, and W1=W2. However for the second positive pulse 611p and the corresponding negative pulse 611n in Pulse Train 1, the amplitudes A1 and A2 respectively are not equal, and their pulse widths W1 and W2, respectively, are also different. That is, pulses 612p and 612n are differently sized.

The positive and the negative pulse 621p and 621n respectively in case of Pulse Train 2 602, are identical to 611p and 611n of Pulse Train1 601. Therefore, the amplitude and pulse width for pulses 611p and 611n are equal. That is, for 611p and 611n, A1=A2, and W1=W2.

The output of the stimulator, as controlled by the microcontroller, can be programmed to vary:

The number of pulses in a pulse train;
The shape of pulses in a pulse train;
The interval between pulse train repetitions;
The duration of each pulse;
The timing and amplitude of pulses in trains;
The desired amount of amperage to be provided to the LES;
The desired amount of potential to be provided to the LES, depending upon the load and the current produced.

Further, the electrical stimulus may have any shape necessary to produce the desired result, including a square, rectangular, sinusoidal, or saw tooth shape.

Optionally, the stimulus may be triggered by a transmitter (not shown) external to the human body, similar to a remote transmitter for a cardiac pacemaker.

Figure 7:
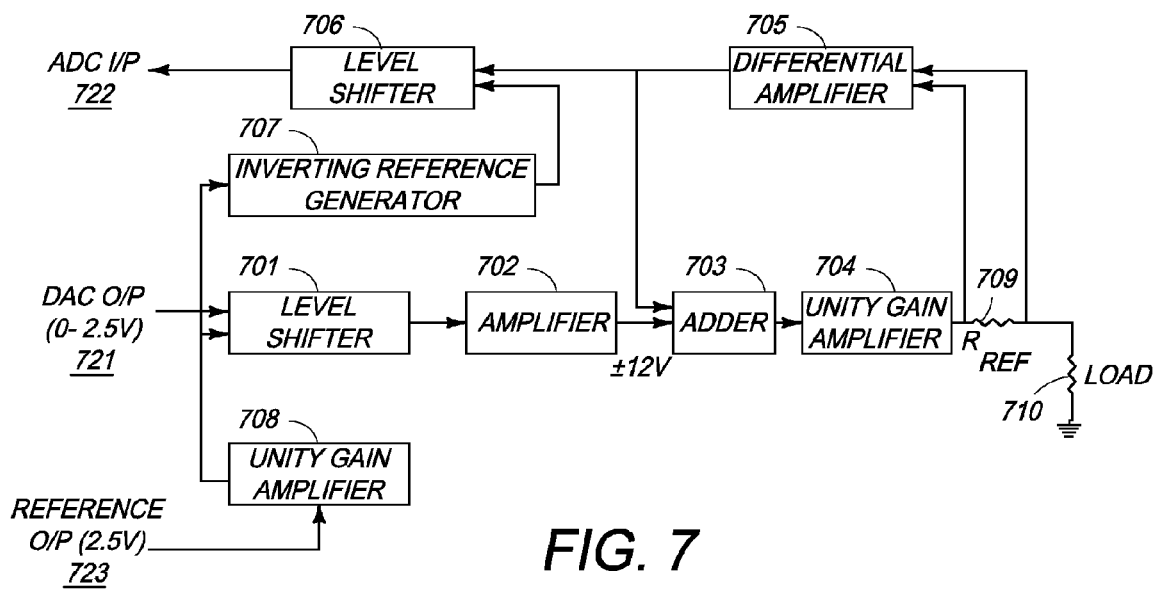
FIG. 7 is a block diagram depicting major components of the stimulator circuit.

FIG. 7 depicts the major components of the stimulator circuit by means of a block diagram. Referring to FIG. 7, output from the microcontroller is fed through a DAC (Digital to Analog Converter) 721 to the stimulator circuit. The DAC output 721, which is 0-2.5V, is then converted to a higher voltage level of ±12V (bipolar) by the level shifter 701. A unity gain amplifier 708 and an amplifier 702 with gain of 5 aids in obtaining this high level shift. The level shifted voltage is then fed into an adder 703, which also receives the reference voltage input from the differential amplifier 705. The output of the adder 703 is again reinforced by means of a unity gain amplifier 704 so that the voltage drop at the resistance $R_{REF}$ 709 does not affect the desired 12V, which is further given to the load 710. The load 710 is actually the resistance of the lower esophageal sphincter muscles, to which the voltage is applied to provide electrical stimulation.

The voltage across the resistance $R_{REF}$ 709 is fed to the differential amplifier 705. The output of the differential amplifier 705 is again level shifted by the level shifter 706 in order to convert it into a positive value, which is supplied as input to an ADC (Analog to Digital Converter) 722. The other input to the level shifter 706 is provided by the inverting reference generator 707 which in turn is fed by the unity gain amplifier 708. The reference voltage received by the unity gain amplifier 708 is the reference output 723 from the microcontroller. The inverting reference generator 707 aids in obtaining a positive value for the ADC input 722. The output from the differential amplifier 705 is also fed to the adder 703, as mentioned earlier, and is used as a feed back to calculate the load resistance and to show the waveform across load.

Figure 8:
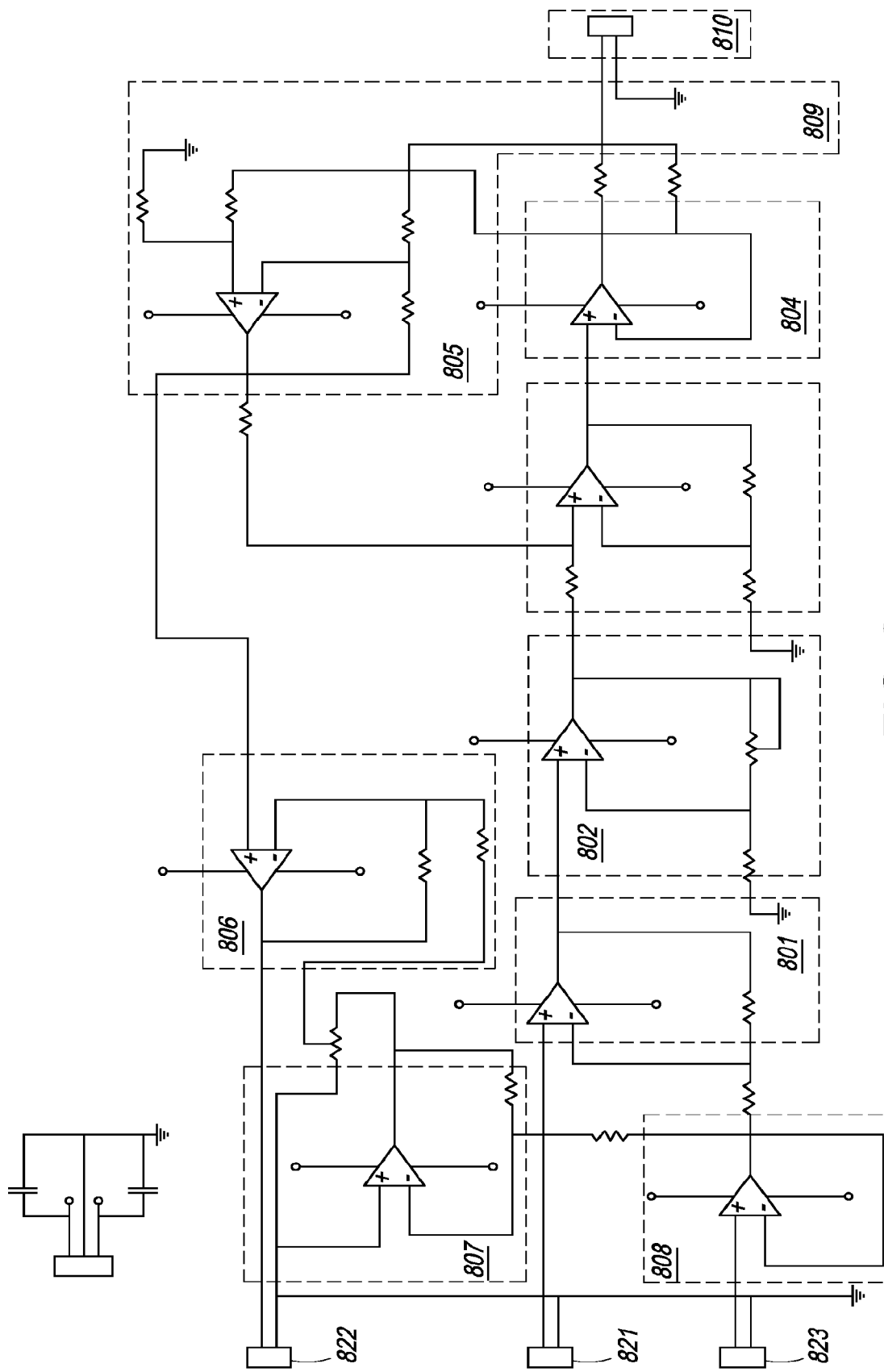
FIG. 8 is a detailed circuit diagram of the stimulator.

The detailed circuit diagram for the stimulator is shown in FIG. 8, wherein 801 through 810 represent the circuit details for the corresponding components 701 through 710 of FIG. 7. Thus, referring to FIG. 8, output from the microcontroller is fed through a DAC 821 to the stimulator circuit. The DAC output 821 is then converted to a higher voltage level by the level shifter 801. A unity gain amplifier 808 and an amplifier 802 aid in obtaining this high level shift. The level shifted voltage is then fed into an adder 803, which also receives the reference voltage input from the differential amplifier 805. The output of the adder 803 is again fed to a unity gain amplifier 804 so that the voltage drop at the resistance $R_{REF}$ 809 does not affect the desired 12V, which is further given to the load 810.

The voltage across the resistance $R_{REF}$ 809 is reinforced by the differential amplifier 805. The output of the differential amplifier 805 is again level shifted by the level shifter 706 in order to convert it into a positive value, which is supplied as input to an ADC 822. The other input to the level shifter 806 is provided by the inverting reference generator 807 which in turn is fed by the unity gain amplifier 808. The reference voltage received by the unity gain amplifier 808 is the reference output 823 from the microcontroller. The inverting reference generator 807 aids in obtaining a positive value for the ADC input 822. The output from the differential amplifier 805 is also fed to the adder, as mentioned earlier, and is used as a feed back to calculate the load resistance and to show the waveform across the load.

Figure 9:
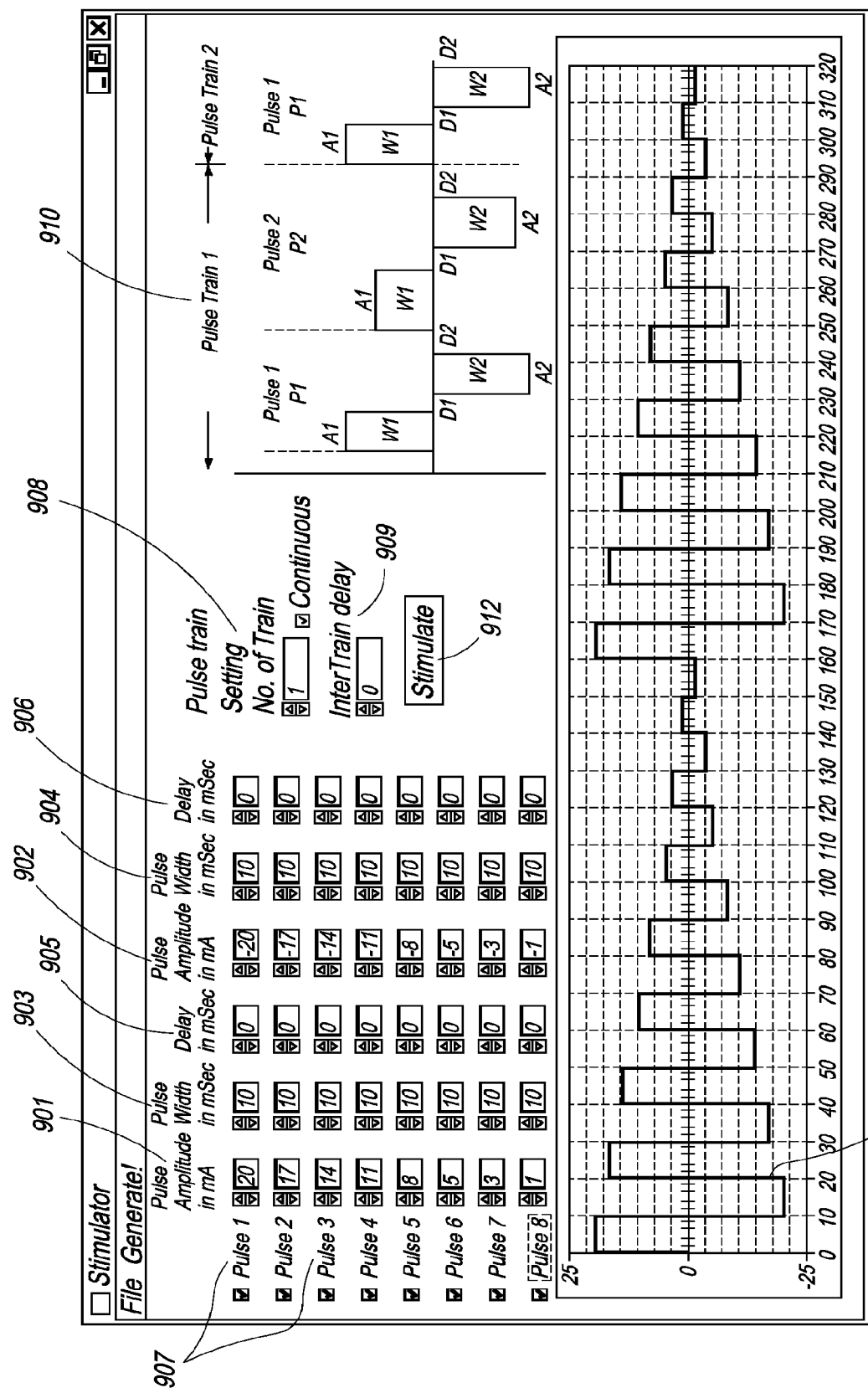
FIG. 9 is a schematic illustration of an exemplary screen shot of the GUI as used with the present invention.

As mentioned previously, the microcontroller unit can be programmed using a computer such that it controls the stimulator to produce electrical pulses in accordance with the esophageal flow sensed by the sensor module. The programming can be done with the help of a suitable program running on the computer that sends simple commands to the microcontroller to set up pulse timing and amplitude. In one embodiment, the computer program code for programming the microcontroller is written using 'C' for Virtual Instrumentation (CVI). The CVI based program running on the computer also provides a graphical user interface (GUI) to make the programming task more convenient and user friendly. An exemplary screen shot of the GUI 900 is illustrated in FIG. 9. Various parameters pertaining to the pulse trains generated by the stimulator may be specified as well as observed using the GUI 900. Referring to FIG. 9, the relevant parameters corresponding to generated pulses include pulse amplitude (in mA) 901 for positive pulses and 902 for negative pulses, pulse duration or width (in mSec) 903 and 904—for positive and negative pulses respectively, delay between pulses (in mSec) 905 and 906—for positive and negative pulses respectively, the number of pulses in a train 907, the number of pulse trains 908, and inter-train delay 909. The GUI 900 also displays a schematic illustration 910 of the pulse train output produced by the stimulator, as well as the continuous waveform 911 for the same. Additionally, the GUI also allows the user to control the generation of pulse stimulus, by means of the 'stimulate' button 912. Thus, even though the timing of generation of pulse stimulus may be preprogrammed in the microcontroller, it can be over-ridden by user command whenever so required. Further, commands from the GUI 900 may be provided to the microcontroller using the serial interface of the computer, or by using any other wired or wireless interface.

Figure 10:
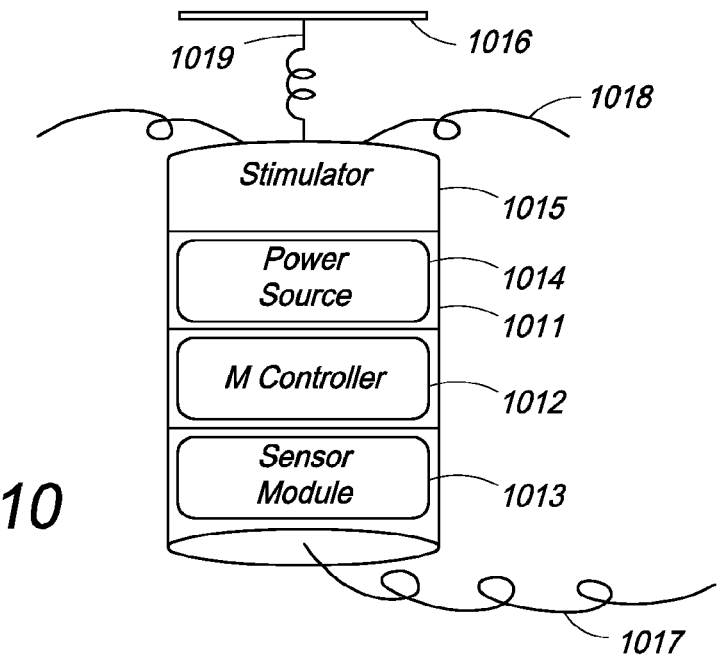
FIG. 10 illustrates an exemplary embodiment of a microdevice that is used as a stimulation system in one embodiment of the present invention.

In one embodiment, the device of the present invention is designed as a 'micro' device with all the major components—the stimulator, the sensor module, the microcontroller and the power source integrated into a single unit, for easy deployment at any desired location in the body. This microdevice is schematically illustrated in FIG. 10. Referring to FIG. 10, the microdevice 1011 contains an outer shell made of a biocompatible, hermetically sealed material such as glass, ceramic or metal or polymers. For this purpose, any material may be selected that keeps moisture out yet allows radiofrequency/electromagnetic or magnetic energy to pass through. The outer shell may also be constructed of an acid corrosion resistant material such as a suitable inert polymer. Examples of such materials include those from the Polyolefin family such as HDPE (high density polyethylene), LLDPE (linear low density polyethylene), and UHMWPE (ultra high molecular weight polyethylene); fluoropolymer materials like PTFETM (poly tetrafluoroethylene), FEPTM (fluorinated ethylene propylene) and others; polymethylpentene, and polysulphons; some elastomers such as thermoplastic polyurethanes and C-Flex type block copolymers that are stable in acidic environments. Additionally the outer shell may be constructed of an acid corrosion resistant metal such as Platinum, Gold, Tantalum, Titanium, or suitable alloys thereof.

The microdevice may be coated with an antimicrobial agent such as an antibiotic or antifungal agent to prevent infection at the time of implantation. Additionally the microdevice may be coated with an immunosuppressent such as steroid, cyclosporine, tacrolimus, azathioprine, mycophenolate mofetil, muromonab CD-3 or antithymocyte globulin to prevent rejection.

The microdevice 1011 further comprises a microcontroller 1012 which stores the algorithm program for sensing and stimulation. In addition, the microcontroller 1012 is capable of receiving data and/or power from outside the body by inductive, radiofrequency (RF), electrical, magnetic, optical or other electromagnetic coupling. In one embodiment, microcontroller 1012 includes an inductive coil for receiving and transmitting RF data and/or power, an integrated circuit (IC) chip for decoding and storing stimulation parameters and generating stimulation pulses (either intermittent or continuous), and additional discrete electronic components such as one or more capacitors, resistors, coils, etc. The microcontroller 1012 also comprises a programmable memory for storing sets of data, and stimulation and control parameters. Programmable memory allows for stimulation and control parameters to be adjusted for each individual patient by means of inductive, radiofrequency (RF), or other electromagnetic coupling, to settings that are safe and efficacious and minimize the discomfort.

The microdevice 1011 may also comprises a sensor module 1013, which senses various physiological parameters through the sensing electrode 1017. The sensor module may be used for sensing any one or more of the various kinds of physiological stimuli, including, but not limited to esophageal peristalsis, esophageal pH, esophageal impedance, esophageal pressure, esophageal electrical activity, LES pressure, LES electrical activity, gastric peristalsis, gastric electrical activity, gastric chemical activity, gastric hormonal activity, gastric temperature, gastric pressure, gastric impedance and gastric pH, duodenal peristalsis, duodenal electrical activity, duodenal chemical activity, duodenal hormonal activity, duodenal temperature, duodenal pressure, duodenal impedance and duodenal pH, blood chemical and/or hormonal activity, vagal or other gastrointestinal neural activity and salivary chemical activity, biliary pressure, biliary electrical activity, biliary chemical activity, pancreatic pressure, pancreatic electrical activity, pancreatic chemical activity, pancreatic sphincter pressure, pancreatic sphincter electrical activity, biliary sphincter pressure, or biliary sphincter electrical activity, mesenteric vascular pressure, mesenteric vascular flow, and mesenteric vascular chemical contents.

The microdevice 1011 further comprises a power source 1014. In one embodiment, the power source 1014 comprises an external power source coupled to microdevice 1011 via a suitable means, such as RF link. In another embodiment, the power source 1014 comprises a self-contained power source utilizing any suitable means of generation or storage of energy. Examples of such a power source include a primary battery, a replenishable or rechargeable battery such as a lithium ion battery, an electrolytic capacitor, and a super- or ultra-capacitor, etc. In case the self-contained power source is replenishable or rechargeable, any suitable means of replenishing or recharging the power source may be used, such as an RF link, an optical link, a thermal link, or any other energy-coupling link.

The microdevice 1011 comprises a stimulator 1015 that is capable of generating a stimulus for stimulating the nerves or smooth muscle in any desired part in the body. The stimulus pulse generated by the stimulator 1015 may be square, rectangular, sinusoidal, or saw tooth. Further, the amperage and frequency of the generated stimulus may be adjusted to levels appropriate to achieve the desired stimulation effect. The desired stimulus pulse is delivered through the stimulation electrode 1018. In one embodiment, the stimulating electrodes 1018 as well as the sensing electrode 1017 are made up of a conducting ceramic, conducting polymer, and/or a noble or refractory metal, such as gold, silver, platinum, iridium, tantalum, titanium, titanium nitride, niobium, stainless steel, or their alloys. The objective of this choice of materials is to minimize corrosion, electrolysis, and damage to the surrounding tissues. In one embodiment, the alloy constituting the sensing and stimulating 1017 electrodes 1018 is a shape memory alloy (SMA) that at body temperature conforms to a pre-designated shape to aid with anchoring or positioning for ideal sensing or stimulation. This makes the sensing and stimulating electrodes ideally conformed for sensing or stimulation at a specific portion of the body.

The microdevice 1011 also comprises an anchoring unit 1016 which helps anchor the microdevice to any given location in the body for short-term or long term implantation. For certain applications, a single electrode is used as the sensing electrode 1017 and the stimulating electrode 1018. For other applications the sensing electrode 1017 and anchoring unit 1016 or the stimulating electrode 1018 and anchoring unit 1016 may be the same element. For still other applications the same element may be used as the sensing electrode 1017, the anchoring unit 1016 and the stimulating electrode 1018. The anchoring unit 1016 is provided with an attachment 1019, which is designed such that it foreshortens after deployment into the body, thereby pulling the microdevice deeper into the particular site in body or snug with the wall and providing better retention. This novel design of the anchoring unit provides for easy and efficient implantation of the microdevice. In addition, pulling the microdevice snug to the wall provides a seal to the puncture site preventing leakage of intraluminal contents and resulting complications.

Figure 11:
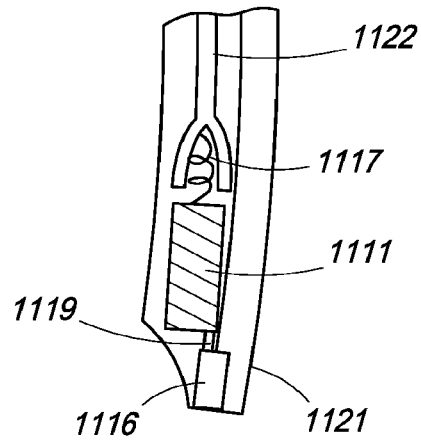
FIG. 11 illustrates an exemplary embodiment of a catheter used for the implantation of the microdevice.

The present invention further provides a novel catheter design, which simplifies the deployment procedure, in addition to providing an effective deployment of the microdevice. FIG. 11 illustrates an exemplary catheter 1100, used for the deployment of the microdevice 1111. The catheter 1100 is designed to pass through the channel of an endoscope or laparoscope or alongside an endoscope over a guide-wire or over an attached track or an external channel. Optionally, single fiber endoscope or wireless optical or imaging devices can be incorporated into the catheter. It can also be radiologically or sterotactically driven to the site of deployment of the microdevice. Optionally, the catheter 1100 is provided with a needle 1121 to create a puncture into the site where the microdevice is to be implanted. In one embodiment, the anchoring unit 1116 can also be used to make the puncture. Further optionally, a suitable fluid such as saline, gonak (HPMC), air or $CO_2$ may be instilled through a port 1123 and the needle 1121 to create a temporary pocket in the wall of the organ where the microdevice is to be deployed. The catheter 1100 is also provided with a pusher 1122 which assists in deployment of the microdevice 1111 at the appropriate site. An optional lumen 1124 is provided for passage of a guidewire to further assist with accurate positioning and deployment of the microdevice 1111.

Figure 12:
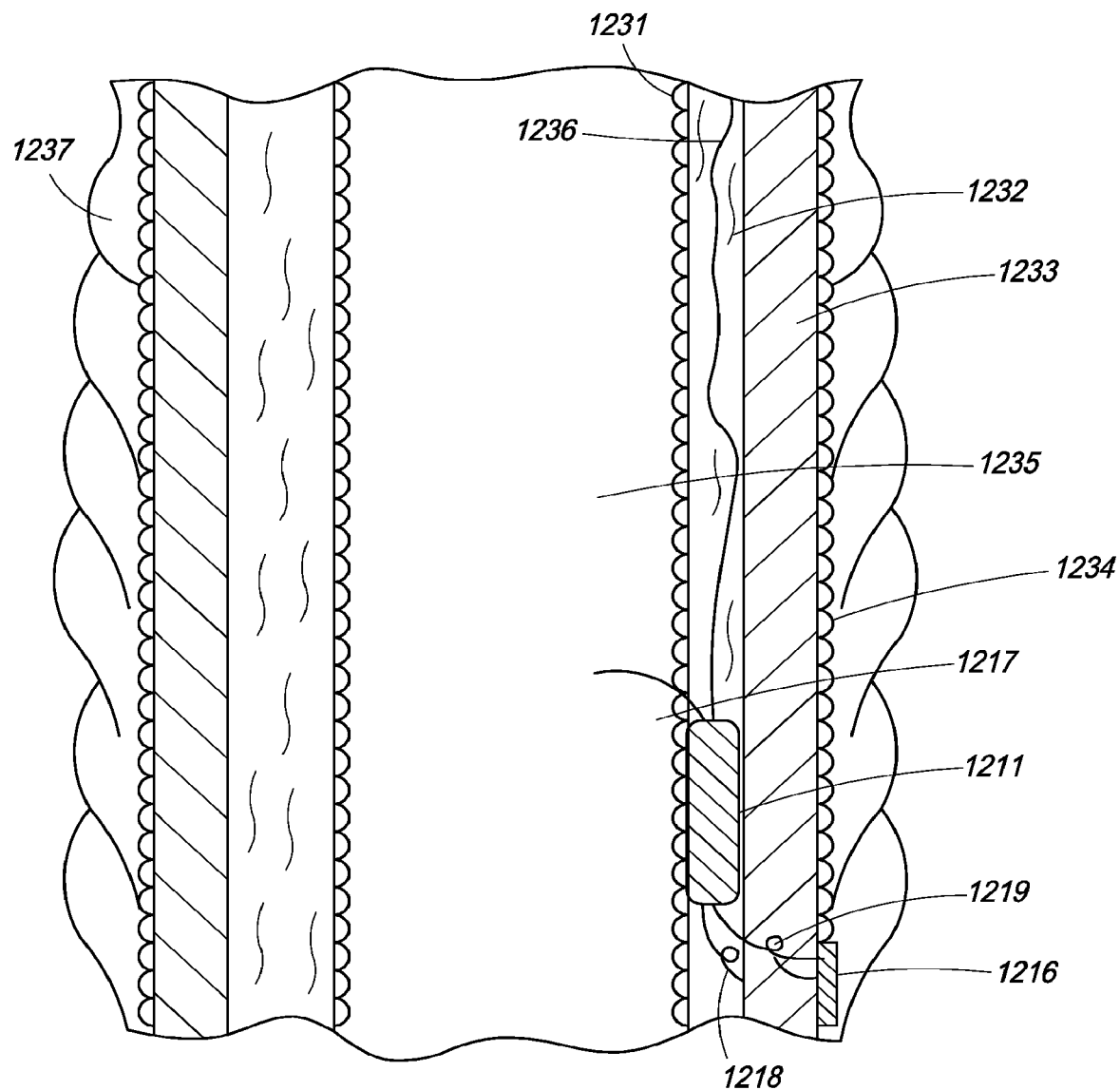
FIG. 12 illustrates an exemplary embodiment of the microdevice implanted in the submucosa of the gastrointestinal tract.

FIG. 12 shows an exemplary deployment of the microdevice 1211 in the submucosa of the gastrointestinal tract using the novel catheter of the present invention. Typical layers of the gastrointestinal tract include the mucosa 1231, submucosa 1232, muscularis propria 1233, serosa 1234 and the lumen 1235. The anchoring unit 1216 is passed through the muscularis propria 1233 to anchor the microdevice 1211 to the wall. This is done because it is the natural tendency of the body to expel any foreign object in the submucosa 1232 into the lumen 1235 over time unless the object is anchored through the muscularis propria 1233 into the serosa 1234. In the exemplary embodiment, the sensing electrodes 1217 are shaped such that after deployment they automatically position in either of the mucosa 1231, submucosa 1232, muscularis propria 1233, and the lumen 1235 to sense physiological changes. The stimulating electrodes 1218 are shaped such that after deployment they automatically position in either submucosa 1232 to stimulate the submucosal nerves 1236 or in muscularis propria 1233 for direct smooth muscle stimulation or in serosa 1234 for stimulating serosal nerves 1237, respectively.

To enable the requisite automated positioning, the various electrodes and/or anchoring unit are preferably made using shape memory technology. In one embodiment, electrodes and/or anchoring unit are physically structured to be positioned in a substantially straight line with the microstimulator, to thereby enable the electrode to pass through the catheter or channel of the endoscope, and, when deployed, the electrode and/or anchoring unit configures into a different shape, such as a hook, J-shape, U-shape, spring, a spiral disc, a spiral loop, a loop, a shape contoured to the implant site, corkscrew, T-shape, ship anchor or other non-linear shape. These various pre-deployment and post-deployment shapes are further described below. Such electrodes and/or anchoring unit preferably comprise a shape memory alloy (SMA), which is also known as a smart alloy, memory metal, or muscle wire and is equivalent to any alloy that conforms to a first pre-defined shape at one temperature (e.g. linear at room temperature) and a second pre-defined shape at a second, higher temperature (e.g. hook, J-shape, corkscrew, U-shape, spring, T-shape, a spiral disc, a spiral loop, a loop, a shape contoured to the implant site, ship anchor or other non-linear shape at internal body temperatures, i.e. 98.7 degrees Fahrenheit).

In certain embodiments, the anchoring unit 1216 may also function as the stimulating electrode 1218 to stimulate the serosal nerves 1237 or the outer longitudinal smooth muscle layer of muscularis propria 1233. In another embodiment, the sensing unit 1217 may also function as the stimulating electrode 1218 to stimulate the submucosal nerves 1236 or the inner circular smooth muscle layer of muscularis propria 1233. In one embodiment, the connecting unit 1219 of the anchoring unit 1216 is made up of shape memory allow (SMA) that foreshortens, thereby pulling and embedding the microdevice 1211 into deep submucosa. This configuration is ideally suited for endoscopic deployment.

Figure 13:
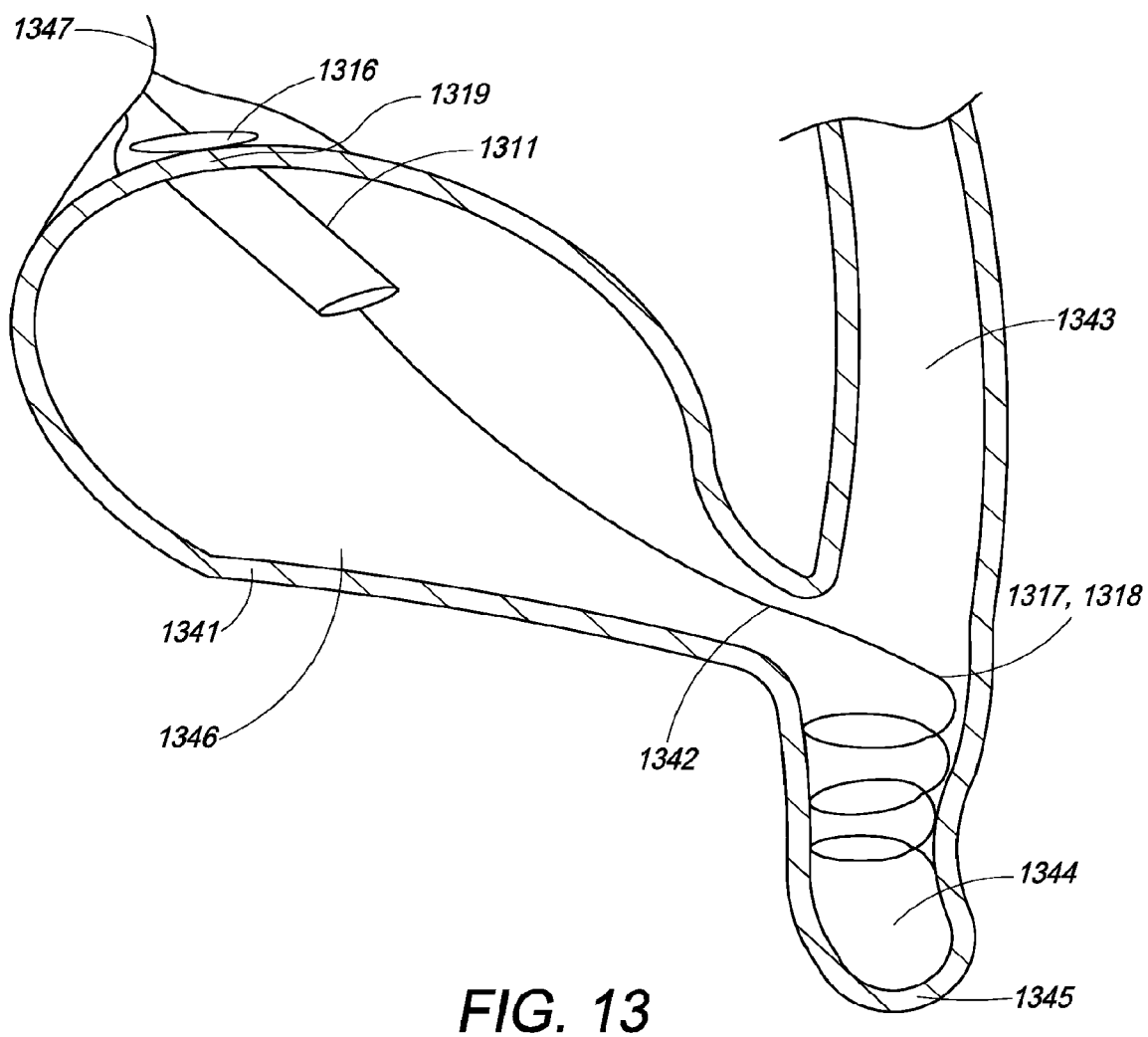
FIG. 13 illustrates an exemplary embodiment of the microdevice implanted in the gallbladder lumen.

FIG. 13 shows another exemplary deployment of the microdevice 1311 in the biliary system using the catheter of the present invention. Typical parts of the biliary system include gallbladder 1341, cystic duct 1342, common hepatic duct 1343, common bile duct 1344, biliary sphincter 1345 and the gall bladder lumen 1346. The microdevice can be implanted using an endoscopic ultrasound, endoscopic retrograde cholangiography (ERC), laparoscopically, surgically or radiologically. During an ERC a guidewire is advanced into the gallbladder and the microdevice catheter is passed into the gallbladder over the guidewire. The anchoring unit 1316 is passed through a puncture in the wall of the gall bladder 1341, thus anchoring the microdevice 1311 to the wall. In this situation the microdevice 1311 hangs freely in the gall bladder lumen 1346.

In one embodiment, the sensing electrodes 1317 are shaped such that after deployment they automatically configure to be positioned in and sense in any one of the cystic duct 1342, CBD 1344 and biliary sphincter 1345 to sense physiological changes in the biliary system. The stimulating electrodes 1317 are shaped such that after deployment they automatically configure to positioned in and stimulate either one of the cystic duct 1342, CBD 1344 or biliary sphincter 1345 to stimulate the biliary system. In certain embodiments, the anchoring unit 1316 may also function as the stimulating electrode 1318 to stimulate serosal nerves 1347 or gall bladder 1341. In another embodiment, the sensing electrode 1317 may also function as the stimulating electrode 1318 to stimulate the biliary system. In the exemplary embodiment, the connecting unit 1319 of the anchoring unit 1316 is made up of SMA that foreshortens, thereby pulling and embedding the microdevice 1311 into the gall bladder wall. The mechanism also seals the puncture in the gall bladder wall, thereby preventing leakage of gall bladder contents into the peritoneal cavity and causing any complications.

It should be appreciated that the sensing function of an electrode and stimulating function of an electrode are happening at different times and, therefore, a single electrode can have both sensing and stimulating functionality. For example, EMG may be monitored in the LES and change in LES EMG may signal a transient relaxation event. Once the microstimulator senses that event it can pulse the LES through the same electrode to abolish the transient LES relaxation. The electrode after finishing the stimulation can than re-assume the sensing function. As long as one does not need to perform sensing and stimulation simultaneously, the same leads may serve both functions.

Figure 14:
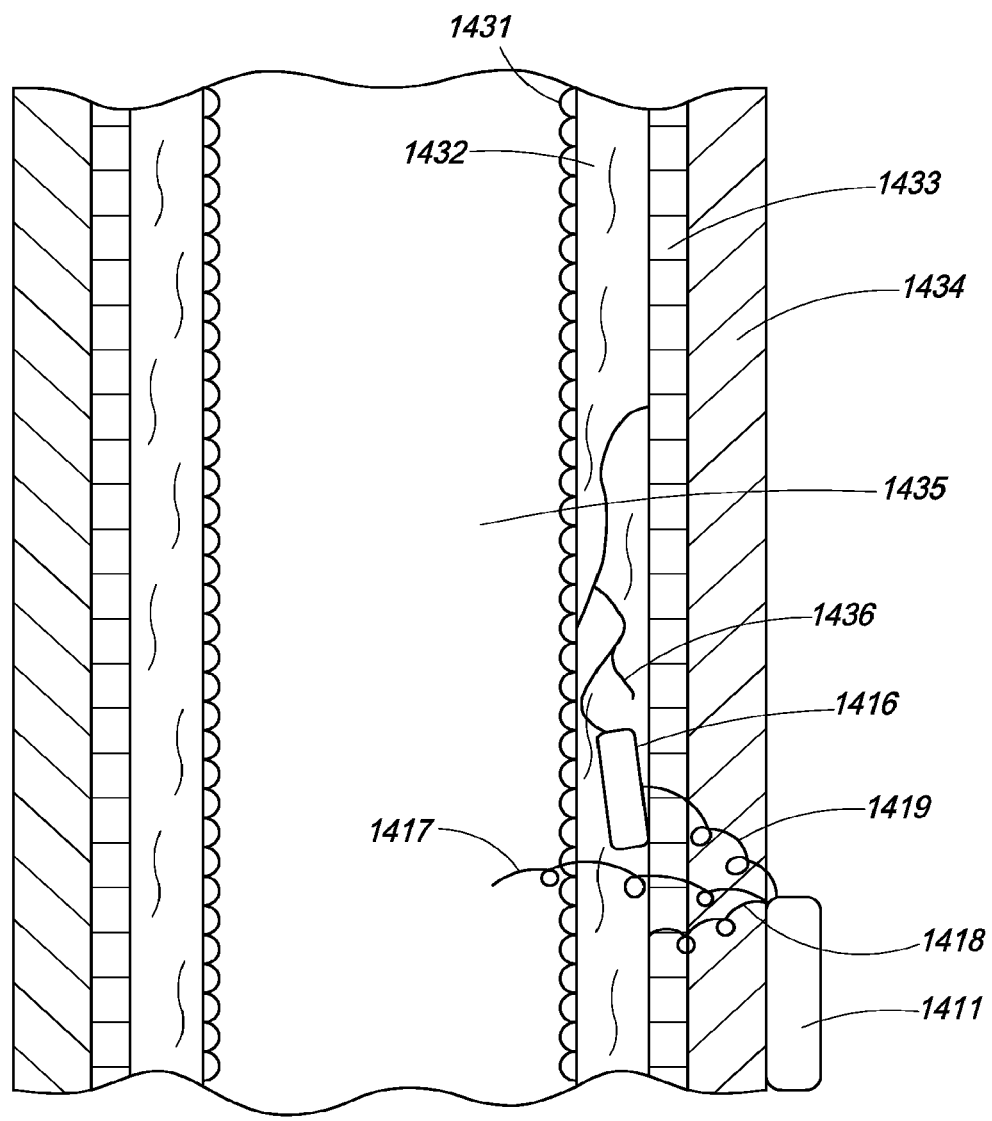
FIG. 14 illustrates an exemplary embodiment of the microdevice implanted on the serosal surface of the gastrointestinal tract.

FIG. 14 shows another exemplary deployment of the microdevice 1411 in the serosa of the gastrointestinal tract using the using the catheter of the present invention. Typical layers of the gastrointestinal tract include the mucosa 1431, submucosa 1432, muscularis propria 1433, serosa 1434 and the lumen 1435. In an exemplary embodiment, the anchoring unit 1416 is passed through the muscularis propria 1433 to anchor the microdevice 1411 to the wall. In this embodiment the microdevice is on the serosal surface of the gastrointestinal tract. In one embodiment, the sensing electrode 1417 is shaped such that after deployment it automatically positions itself either one of the mucosa 1431, submucosa 1432, muscularis propria 1433, serosa 1434 or the lumen 1435 to sense physiological changes. The stimulating electrode 1418 are shaped such that after deployment it automatically positions itself in either the submucosa 1432 to stimulate the submucosal nerves 1436, or in the muscularis propria 1433 for direct smooth muscle stimulation or the serosa 1434 for stimulating the serosal nerves 1437, respectively. In certain embodiments, the anchoring unit 1416 may also function as the stimulating electrode 1418 to stimulate the submucosal nerves 1436 or the inner circular smooth muscle layer of muscularis propria 1433. In another embodiment, the sensing unit 1417 may also function as the stimulating electrode 1418 to stimulate submucosal nerves 1436 or the inner circular smooth muscle layer of muscularis propria 1433. The connecting unit 1419 of the anchoring unit 1416, in one embodiment, is made up of SMA that foreshortens, thereby pulling and embedding the microdevice into the serosa. This configuration is ideally suited for laparoscopic or radiological placement.

Figure 15D:
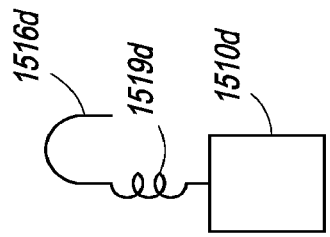
FIG. 15d illustrates a fourth exemplary configuration of the anchoring system.
Figure 15C:
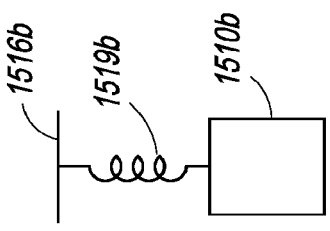
FIG. 15c illustrates a third exemplary configuration of the anchoring system.
Figure 15B:
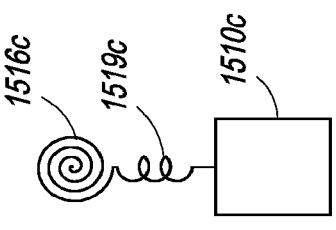
FIG. 15b illustrates a second exemplary configuration of the anchoring system.
Figure 15A:
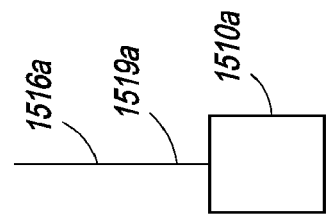
FIG. 15a illustrates a first exemplary configuration of the anchoring system.
Figure 15H:
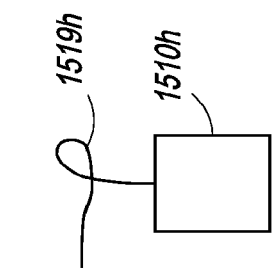
FIG. 15h illustrates an eighth exemplary configuration of the anchoring system.
Figure 15G:
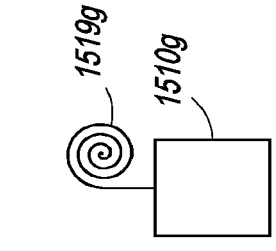
FIG. 15g illustrates a seventh exemplary configuration of the anchoring system.
Figure 15F:
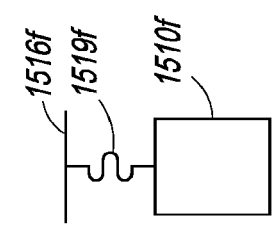
FIG. 15f illustrates a sixth exemplary configuration of the anchoring system.
Figure 15E:
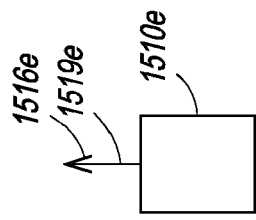
FIG. 15e illustrates a fifth exemplary configuration of the anchoring system.

FIGS. 15*a* through 15*h* illustrate various configurations of the anchoring unit. FIG. 15*a* illustrates the pre-deployed position of the anchor 1516*a*, wherein the anchor is positioned straight to facilitate puncture of the gastrointestinal wall. As mentioned previously, the anchor itself may be used to make the puncture or a separate needle may be used for the purpose. In this configuration, the connecting unit 1519*a* which connects the anchoring unit 1516*a* to the microdevice 1510*a* is also positioned straight. FIG. 15*b* illustrates an exemplary configuration of the anchor 1516*b* after deployment. As can be seen from FIG. 15*b*, after deployment the anchor 1516*b* assumes the shape of a T-fastener, with the connecting unit 1519*b* which connects to the microdevice 1510*b* becoming spirally coiled. Alternatively, as illustrated in FIG. 15*e*, the anchor 1516*e* assumes the shape of a ship anchor after deployment. In this embodiment, the connecting unit 1519*e* which connects the anchoring unit 1516*e* to the microdevice 1510*e* remains straight and may not foreshorten.

In an exemplary embodiment, the anchoring unit is made up of shape memory alloy (SMA), which provides flexibility of shape, as discussed above. Thus, in alternate configurations, post deployment the anchor may assume several different shapes, depending upon the site of deployment. Thus as shown in FIG. 15*c*, the anchoring unit 1516*c* assumes the shape of a spiral disc, while the connecting unit 1519*c*, which connects to the microdevice 1510*c*, becomes spirally coiled. In FIG. 15*d* the anchoring unit 1516*d* assumes the shape of a hook, with the connecting unit 1519*d* which connects to the microdevice 1510*d* becoming spirally coiled. In FIG. 15*f* the anchoring unit 1516*f* and the connecting unit 1519*f* together assume the shape of a T bar, where the connecting unit 1519*f* is coiled. In FIG. 15*g*, the anchoring unit 1519*g* connected to the microdevice 1510*g* assumes a spiral loop shape, and in FIG. 15*h* the anchoring unit 1519*h* connected to the microdevice 1510*h* assumes the shape of a loop. These various shapes per se result in shortening of the anchoring unit 1519 pulling the device deeper into or snug with the wall of the organ. It may be noted that more than one fasteners or anchors may be used, depending upon the requirement of the application. Further, the anchors may be used in more than one configuration depending on the organ or site of implantation. In addition the attachment (connecting unit) of the anchoring unit can also be made of SMA, as mentioned previously, and can foreshorten by coiling. The coiling is illustrated by 1519*b*, 1519*c* and 1519*f* in FIGS. 15*b*, 15*c*, and 15*f*, respectively, and it helps to pull the microdevice deeper into the wall of the organ.

FIGS. 16*a* through 16*h* show various configurations of the sensing electrode. FIG. 16*a* illustrates the pre deployed position, where the sensing unit or electrode 1617a is positioned straight to facilitate insertion and delivery of the microdevice 1610a through a catheter into the lumen or wall of the organ. One of the possible post deployment states is shown in FIG. 16b. Referring to FIG. 16b, the electrode 1617b assumes a spiral shape after the microdevice 1610b is deployed. The spiral shape is especially suitable when sensing at a tubular lumen site such as the cystic duct or common bile duct, as shown in FIG. 16c. Referring to FIG. 16c, the microdevice 1610c is seen firmly anchored inside the gall bladder 1650c, with the help of the anchoring device 1616c, while the sensing electrode 1617c is coiled in the bile duct 1652c. In another embodiment shown in FIG. 16d, the sensing electrode 1617d assumes an acute angular configuration after the microdevice 1610d is deployed. In FIG. 16f, the sensing electrode 1617f connected to the microdevice 1610f assumes a hook configuration. The two configurations illustrated in FIGS. 16d and 16f are ideal for sensing intraluminal physiology at the gastroesophageal junction, which is depicted in FIG. 16e.

Referring to FIG. 16e, the microdevice 1610e is deployed with the help of the anchoring device 1616e inside the EG junction 1660e, while the sensing electrode 1617e assumes an angular configuration for optimum sensing. In the exemplary embodiment, the microdevice 1610e is inserted into the submucosa per-orally via an endoscope and after deployment the SMA in the electrode assumes an angular or hook configuration bringing the electrode closer to the mucosa or the EG junction 1660e. This provides for increased sensitivity of detection of physiological changes near the junction or esophageal sphincter. In another embodiment illustrated in FIG. 16g, the microdevice 1610g is of cylindrical shape, and one surface of the cylinder comprises a disc sensor or electrode 1617g. This configuration is ideally suited for sensing at a large surface area in the mucosa, submucosa or muscularis. FIG. 16h shows the microdevice 1610h implanted in the submucosa 1662h with the help of the anchoring unit 1616h. The disc sensor 1617h of the microdevice 1610h in this configuration senses physiological changes from the inner circular muscle layer of the esophagus.

FIG. 17 shows various configurations of the stimulating electrode. In the pre deployed position illustrated in FIG. 17a, the stimulating electrode 1718a is straight, which facilitates insertion and delivery of the microdevice 1710a through a catheter into the lumen or wall of the organ. One of the post deployment states is illustrated in FIG. 17b, where the stimulating electrode 1718b assumes a spiral shape. This shape is especially useful for stimulation in a tubular lumen such as the cystic duct, common bile duct, urethra or a blood vessel. FIG. 17c illustrates the placement of the microdevice 1710c and the stimulating electrode 1718c in the bile duct 1750c.

In another embodiment shown in FIG. 17d, the stimulating electrode 1718d assumes a hook configuration after the microdevice 1710d is deployed. In FIG. 17f, the stimulating electrode 1718f assumes a double hook configuration after deployment of the microdevice 1710f It may be noted that the curvature of the hook may be designed accordingly to stimulate the deeper longitudinal smooth muscles or more superficial circular smooth muscle. For example, while a J-shaped hook configuration may be ideally suited to stimulate the deeper longitudinal smooth muscles, a U-shaped hook configuration is ideally suited to stimulate the more superficial circular smooth muscle. FIG. 17e illustrates the microdevice 1710e with a J-shaped stimulating electrode 1718e deployed with the help of the anchoring unit 1716e into a submucosal wall 1760e.

In another embodiment shown in FIG. 17g, the microdevice 1710g is of cylindrical shape, and one surface of the cylinder comprises a disc stimulating electrode 1718g. This configuration is ideally suited for stimulating a large surface area. FIG. 17h shows the microdevice 1710h implanted with the help of the anchor 1716h in the submucosa 1770h, with the disc stimulator 1718h stimulating the inner circular muscle layer of the esophagus.

FIG. 18 shows various configurations of the anchoring system in a puncture needle. In the pre-deployed position illustrated in FIG. 18a, a ship anchor shaped anchoring system in its pre-deployment shape 1816a is housed in the needle 1821a with a slit to house the connecting unit 1819a. Referring to FIG. 18b, the needle 1821b, with connecting unit 1819b, is pushed through the wall of the organ 1810b carrying the anchor 1816b with it. On deployment as shown in FIG. 18b, the anchor comes out of its housing at the end of the needle 1821b and opens to its post-deployment position 1816b. The needle is then withdrawn and the open anchor 1816b anchors to the wall while the connecting unit 1819b comes out of the slit freeing the deployed anchor 1816b from the needle 1821b.

Figure 18A:
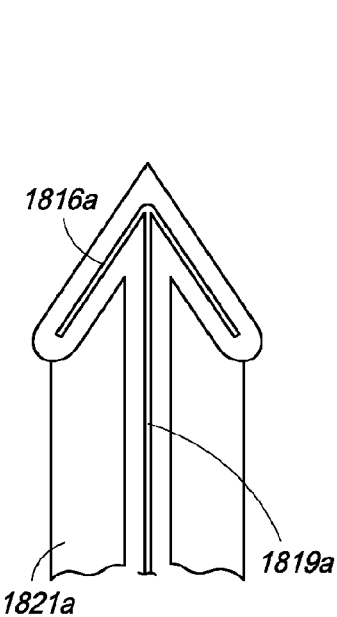
FIG. 18a illustrates a first exemplary configuration of the anchoring system pre-deployment in the puncture needle.
Figure 18B:
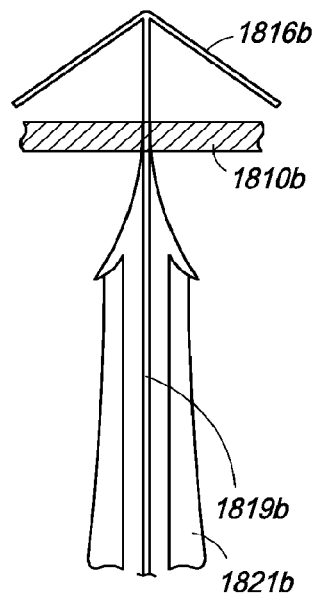
FIG. 18b illustrates a first exemplary configuration of the anchoring system post-deployment out of the puncture needle.
Figure 18E:
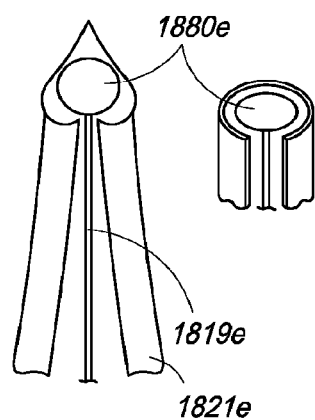
FIG. 18e illustrates a third exemplary configuration of the anchoring system pre-deployment in the puncture needle.
Figure 18C:
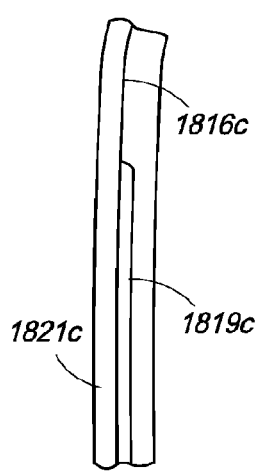
FIG. 18c illustrates a second exemplary configuration of the anchoring system pre-deployment in the puncture needle.
Figure 18D:
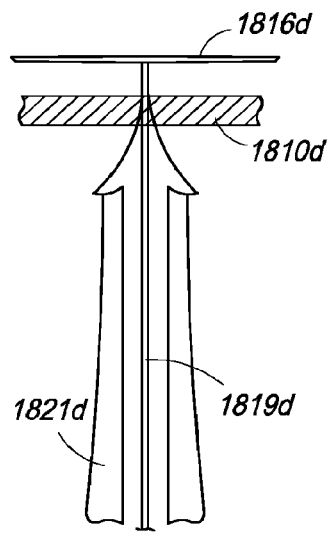
FIG. 18d illustrates a second exemplary configuration of the anchoring system post-deployment out of the puncture needle.

In another embodiment shown in FIG. 18c, a T-bar shaped anchoring system in its pre-deployment shape 1816c is housed in the needle 1821c with a slit to house the connecting unit 1819c. Referring to FIG. 18d, the needle 1821d is pushed through the wall of the organ 1810d carrying the anchor 1816d with it. On deployment as shown in FIG. 18d, the anchor 1816d comes out of its housing at the end of the needle 1821d and opens to its post-deployment position 1816d. The needle is than withdrawn and the deployed anchor 1816d anchors to the wall while the connecting unit 1819d comes out of the slit freeing the deployed anchor 1816d from the needle 1821d.

Figure 18F:
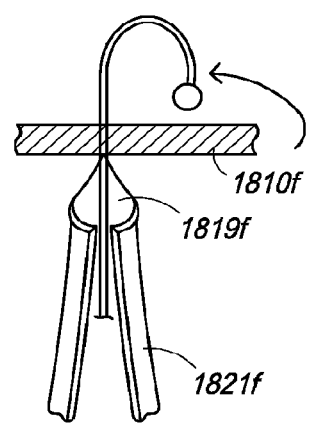
FIG. 18f illustrates a third exemplary configuration of the anchoring system post-deployment out of the puncture needle.

In a third embodiment shown in FIG. 18e, a hook anchoring system which is straight in its pre-deployment shape 1819e is housed in the needle 1821e with a slit. A small spherical knob 1880e holds the anchor and connecting unit 1819e in position in the needle 1821e preventing slippage of the anchor. Referring to FIG. 18f, the needle 1821f is pushed through the wall of the organ 1810f carrying the anchor 1819f with it. On deployment as shown in FIG. 18f, the knob comes out of its housing at the end of the needle 1821f and the anchor assumes its post-deployment hook position 1819f. The needle is then withdrawn and the deployed anchor 1819f anchors to the wall and comes out of the slit thus freeing the deployed anchor 1819f from the needle 1821f.

The aforementioned features of the present invention allow a physician for easy and expeditious deployment of the microdevice in the desired location. For example, if the microdevice is required to be deployed into the submucosa of the lower esophageal sphincter to treat various gastrointestinal disorders, then an exemplary procedure for deployment is illustrated in FIG. 19. Referring to FIG. 19a, in the first step of the procedure, the microdevice 1902a is positioned within a catheter 1901a, which is passed through the channel of an endoscope into the distal esophagus. In the predeployment position, the anchoring unit 1905a, the sensing electrode 1906a and the stimulating electrode 1907a are all in a straight line allowing for easy passage through the endoscope. In the next step, shown in FIG. 19b, a transmural puncture is made through the lower esophageal wall 1903b, thereby placing the catheter 1901b and microdevice 1902b in a position for deployment. A submucosal pocket 1904b is optionally created using a saline injection for ease of deployment Referring to FIG. 19c, the microdevice 1902c is pushed out of the catheter into the submucosal space while the anchoring unit 1905c is pushed transmurally into the serosal layer and the microdevice 1902c is deployed. The anchoring unit 1905c in the deployed position takes one of the post-deployment shapes, thereby anchoring the stimulators to the esophageal wall. After deployment, the attachment element of the anchoring unit 1905c, the sensing electrode 1906c and the stimulation electrode 1907c conform into their pre determined post-deployment position, thus pulling the microdevice 1902c deeper into the esophageal wall, and positioning the sensing electrode 1906c and stimulation electrode 1907c in their desired location. The puncture site generally heals in a few days, resulting in permanent implantation of the microdevice into the esophageal submucosa. Optionally, the puncture site may be closed with a clip, suture or sealed with a sealant or glue to expedite closure.

FIGS. 20a and 20b depict a procedure similar to the one depicted in FIGS. 19a through 19c, except performed in the gallbladder using an endoscope. A catheter containing the microdevice 2002a is used to deliver the microdevice 2002a to the implant site, puncture the gallbladder wall 2006a and deploy the anchor unit 2005a. Referring to FIG. 20b, the anchor unit 2005b conforms to a post deployment shape, thereby pulling the microdevice 2002b into the gallbladder 2006b wall and securing it thereto. After deployment the stimulation electrode 2007b conforms into its pre determined post-deployment spiral shape in the common bile duct.

It may be noted that apart from the method described above, the microdevice of the present invention along with the stimulating or sensing electrodes can also be placed by conventional surgical, laparoscopic, endoscopic radiological or other minimally invasive surgical techniques. Further, conventional electrode stimulation devices may be used in the practice of this invention.

Further, an evaluation of the physical effects induced by the proper operation of the present invention may be made by inspection with an X-ray, ultrasound, CAT scan or MRI or by insertion of a manometer catheter to measure pressures in the esophagus, stomach or the lower esophageal sphincter, a pH or impedance catheter to measure actual reflux events, etc.

While there has been illustrated and described what is at present considered to be a preferred embodiment of the present invention, it will be understood by those skilled in the art that various changes and modifications may be made, and equivalents may be substituted for elements thereof without departing from the true scope of the invention. In addition, many modifications may be made to adapt a particular situation or material to the teachings of the invention without departing from the central scope thereof. Therefore, it is intended that this invention not be limited to the particular embodiment disclosed as the best mode contemplated for carrying out the invention, but that the invention will include all embodiments falling within the scope of the appended claims.

I claim:

1. An electrode coupled to an anchoring unit comprising:
    an electrode; and
    an anchoring unit coupled to said electrode, wherein said anchoring unit comprises:
        a pre-deployment shape; and
        a post deployment shape, wherein said post deployment shape is different than the pre-deployment shape, wherein said anchoring unit is configured to attach said electrode to human tissue by puncturing said tissue at a puncture site, foreshortening upon deployment in the tissue to pull the electrode deeper into said tissue, and, upon being pulled deeper into said tissue, sealing said puncture site.

2. The electrode of claim 1, wherein said anchoring unit is further used to facilitate puncture at an implant site for deployment of said electrode.

3. The electrode of claim 1, wherein, upon deployment of said anchoring unit, a shape of said anchoring unit changes to a predetermined shape.

4. The electrode of claim 1, wherein said predetermined shape is determined based upon an implant site.

5. The electrode of claim 1, wherein the post-deployment shape of said anchoring unit is any one of a T-bar, a ship anchor, a spiral disc, a hook, a spiral loop, a loop or any non-linear shape capable of anchoring.

6. The electrode of claim 1, wherein the electrode is a stimulating electrode and is integrally formed with said anchoring unit.

7. The electrode of claim 6, wherein the post deployment shape of said anchoring unit is any one of a spiral shape, a hook, a double hook, a J-shape or a U-shape.

8. The electrode of claim 1, wherein the electrode is a sensing electrode and is integrally formed with said anchoring unit.

9. The electrode of claim 8, wherein the post deployment shape of said anchoring unit is any one of a spiral shape, an acute angular shape, a J-shape, a U-shape or a hook.

10. The electrode of claim 8, wherein said anchoring unit is also used to detect changes in physiological parameters.

11. The electrode of claim 6 where the anchoring unit and stimulating electrode are made of shape memory alloys.

12. The electrode of claim 8 where the anchoring unit and sensing electrode are made of shape memory alloys.

13. The electrode of claim 10, wherein said physiological parameters include at least one of pH, pressure, peristalsis, temperature, impedance, motion, flow, electrical activity, chemical activity, hormonal activity, and neural activity or muscular activity.

* * * * *